United States Patent
Hawkins et al.

(10) Patent No.: US 10,046,815 B2
(45) Date of Patent: Aug. 14, 2018

(54) WEAR MONITORING DEVICE AND METHOD OF MONITORING UNDERCARRIAGE AND ROLLER WEAR

(71) Applicant: WearPro Incorporated, Tucson, AZ (US)

(72) Inventors: Bradley E. Hawkins, Tucson, AZ (US); Christopher N. Dewitt, Pekin, IL (US)

(73) Assignee: Wearpro Incorporated, Tucson, AZ (US)

( * ) Notice: Subject to any disclaimer, the term of this patent is extended or adjusted under 35 U.S.C. 154(b) by 471 days.

(21) Appl. No.: 13/835,626

(22) Filed: Mar. 15, 2013

(65) Prior Publication Data

US 2013/0255354 A1 Oct. 3, 2013

Related U.S. Application Data

(60) Provisional application No. 61/616,110, filed on Mar. 27, 2012.

(51) Int. Cl.
  *B62D 55/08* (2006.01)
  *B62D 55/15* (2006.01)
  (Continued)

(52) U.S. Cl.
  CPC ............. *B62D 55/08* (2013.01); *B62D 55/15* (2013.01); *B62D 65/00* (2013.01); *G01N 3/56* (2013.01); *Y10T 29/49002* (2015.01)

(58) Field of Classification Search
  CPC .......... G01N 3/56; B62D 55/08; B62D 65/00; B62D 55/15; Y10T 29/49002

(Continued)

(56) References Cited

U.S. PATENT DOCUMENTS

| | | | | |
|---|---|---|---|---|
| 3,102,759 A | * | 9/1963 | Stewart | B61F 15/02 384/276 |
| 4,163,208 A | * | 7/1979 | Merz | B60C 23/007 200/61.25 |

(Continued)

FOREIGN PATENT DOCUMENTS

| | | |
|---|---|---|
| WO | 2011131826 A1 | 10/2011 |
| WO | WO 2011131826 * | 10/2011 |

OTHER PUBLICATIONS bushing-definition from the Merriam-Webster Online Dictionary, Merriam-Webster Online Dictionary, Apr. 2009.*

*Primary Examiner* — John Fitzgerald
*Assistant Examiner* — Truong D Phan
(74) *Attorney, Agent, or Firm* — Robert D. Atkins; Patnet Law Group: Atkins and Associates, P.C.

(57) ABSTRACT

An undercarriage monitoring device has a roller assembly including a fixed roller component and a bushing. An opening is formed within the fixed roller component. A first sensor is disposed within the opening of the fixed roller component over the bushing. The first sensor is configured to sense a first physical characteristic of the bushing. The fixed roller component is a shaft or a housing. The first sensor is a temperature sensor or a Hall effect sensor. A magnet is disposed on the roller assembly. A second sensor is disposed within the opening of the fixed roller component over the bushing. The second sensor is configured to sense a second physical characteristic of the bushing. A data transmitting device is coupled to the first sensor. Data is collected from the sensor. The data collected from the sensor is transmitted to a receiving device.

25 Claims, 11 Drawing Sheets

(51) Int. Cl.
*G01N 3/56* (2006.01)
*B62D 65/00* (2006.01)

(58) Field of Classification Search
USPC .............................. 340/682; 384/448; 73/7
See application file for complete search history.

(56) References Cited

U.S. PATENT DOCUMENTS

| | | | |
|---|---|---|---|
| 4,348,665 A * | 9/1982 | Rode et al. .................. | 340/682 |
| 5,198,763 A | 3/1993 | Konishi | |
| 5,451,110 A * | 9/1995 | Gams et al. .................. | 384/624 |
| 5,562,348 A * | 10/1996 | Link ..................... | B60G 11/12 |
| | | | 267/267 |
| 5,581,180 A * | 12/1996 | Ito .......................... | B61B 12/06 |
| | | | 324/207.11 |
| 6,080,982 A * | 6/2000 | Cohen .................. | F16C 17/246 |
| | | | 250/227.11 |
| 6,206,573 B1 | 3/2001 | Miller et al. | |
| 6,435,629 B1 | 8/2002 | Egle et al. | |
| 2003/0209052 A1* | 11/2003 | Ebi ..................... | 73/7 |
| 2006/0243839 A9 | 11/2006 | Barscevicius et al. | |
| 2008/0234964 A1* | 9/2008 | Miyasaka .............. | G01H 1/003 |
| | | | 702/113 |
| 2010/0139993 A1* | 6/2010 | Sebright ................ | B62D 55/21 |
| | | | 180/6.7 |
| 2012/0227471 A1* | 9/2012 | Smith ................ | G01N 35/1011 |
| | | | 73/61.59 |

* cited by examiner

WEAR MONITORING DEVICE AND METHOD OF MONITORING UNDERCARRIAGE AND ROLLER WEAR

CLAIM TO DOMESTIC PRIORITY

The present application claims the benefit of U.S. Provisional Application No. 61/616,110, filed Mar. 27, 2012, which application is incorporated herein by reference.

FIELD OF THE INVENTION

The present invention relates in general to undercarriage structures for mining and construction equipment, more particularly, to a method of monitoring the wear on an undercarriage.

BACKGROUND OF THE INVENTION

Mining, construction, forestry, agriculture, landscaping, and material handling industries use a variety of heavy equipment for moving earth and other materials. Hydraulic and electric excavators, backhoes, shovels, and drills are examples of equipment commonly used at, for example, mining or construction sites. The pieces of equipment are heavy-duty equipment, which are mobile and some are capable of moving thousands of kilograms of material at a time. The drive system underneath heavy equipment may include axles with wheels or a track-type undercarriage. A track undercarriage is used to move the heavy equipment and large amounts of material over many types of terrain. Track undercarriages are intended to operate on a variety of terrain conditions and can handle a higher operating weight capacity than comparably sized wheeled assemblies.

Track undercarriages include a track located on each side of a piece of heavy equipment underneath the equipment in a similar location to where wheels are located on wheeled equipment. A track undercarriage is used in place of wheels and operates with a drive mechanism to rotate the track to propel the heavy equipment. Each track on either side of the equipment rotates around an oblong undercarriage frame. The track is made up of a series of individual track shoes linked together in a continuous chain. The track undercarriage includes a series of rollers which allow the track to rotate about the undercarriage frame. Rollers include lower rollers or track rollers, upper rollers or carrier rollers, and idler rollers.

The track rotates around an undercarriage frame and is driven by a sprocket. The sprocket is located on one end of the track, typically the rear, and an idler roller supports the opposite end of the track, typically the front. In between the idler and sprocket, a plurality of rollers supports the undercarriage frame and rotates as the track rotates around the undercarriage frame. Rollers provide a low friction surface for the track to move along as the heavy equipment moves along the terrain. Rollers can be located above and below the undercarriage frame on the track. A track moves over the sprocket, over the upper rollers, around the idler at the front of the undercarriage, then under the lower rollers where the track also contacts the ground. An undercarriage typically includes at least one upper roller and several lower rollers. A large shovel, for example, may have two upper rollers, and idler roller, and seven or eight lower rollers. The rollers are load bearing, with some rollers being stressed by the weight of the heavy equipment more than other rollers. The rollers are metal and are typically made of steel and include metal bushings or bearings, typically made of bronze, to reduce friction between parts of the roller assembly.

The roller bushings are located inside the roller assembly and are lubricated in order to allow rollers to rotate with less friction. Roller assemblies may be designed with the bushing fixed, for example, within an end cap in which the roller rotates within the bushing. In an alternative design, the bushing is fixed within the roller body and both the bushing and roller body rotate around a shaft. Ideally, roller assemblies and bushings are well-lubricated and to maintain a low-friction contact surface between the bushing and the roller or between the bushing and shaft. Inadequate lubrication of the contact surfaces increases friction between the bushing and roller assembly which wears down the bushing eventually causing damage to the roller assembly. Even with adequate lubrication, bushings are subject to stress from contact with the roller or shaft and wear out over time. Because bushings and lubricant are internal to a roller assembly, the wear status of the bushings and amount of lubricant within the roller assembly are difficult to monitor.

Roller assemblies within a track undercarriage typically fail due to lack of adequate lubrication. Without adequate lubrication, friction between the rollers and bushings or bushing and shaft increases substantially and causes wear to the components. One indicator of inadequate lubrication is increased heat within the roller assembly. A current approach to monitoring rollers requires a person to measure the temperature of the rollers by walking next to the equipment as the equipment is driven and take periodic temperature readings of the rollers using a laser-sighted infrared gun-style thermometer. The current approach is dangerous for the person taking temperature measurements, because the measurement device requires the person to remain in close proximity to the heavy equipment while the equipment is operating. Further, manual monitoring of roller temperature requires expensive labor, and roller temperature is simply not monitored during everyday operation of the heavy equipment. Another approach to managing a track undercarriage is to inspect and repair components during a pre-scheduled preventative maintenance of the equipment. Often, lubricant and bushings wear out or problems occur before the periodic maintenance.

Without constant monitoring of the roller assemblies on a track undercarriage, lubricant problems go unnoticed and bushings tend to wear down completely before the wear is noticed leaving rollers without any bushings. If a bushing wears down completely and a roller continues to run without a bushing, damage occurs to the roller as the roller contacts other surfaces within the roller assembly. The metal on metal or steel on steel contact between the roller and other roller assembly components results in the surface of the roller and other components to wear and deteriorate beyond the point at which the parts can be repaired. Eventually, a roller without lubricant or a bushing will wear down and stop turning altogether. A track undercarriage is likely to break down at the point of use when a roller stops turning unexpectedly. Equipment that breaks down at a work site creates additional hazards and maintenance problems in addition to adding cost to repairs and replacements. However, if lubricant problems or bushing wear is caught early, a roller assembly can be repaired. Repair of roller assembly components is less expensive than replacement with a new roller assembly.

SUMMARY OF THE INVENTION

A need exists for a monitoring device for wear on undercarriage components, such as a roller. In one embodiment, the present invention is a method of making an undercarriage monitoring device comprising the steps of providing a roller assembly including a fixed roller component and a bushing, forming an opening within the fixed roller component, and disposing a first sensor within the opening of the fixed roller component over the bushing. The first sensor is configured to sense a first physical characteristic of the bushing.

In another embodiment, the present invention is an undercarriage monitoring device comprising a roller assembly including a fixed roller component and a bushing and a first sensor disposed on the fixed roller component over the bushing. The first sensor is configured to sense a first physical characteristic of the bushing.

In another embodiment, the present invention is an undercarriage monitoring device comprising a first roller component and a sensor disposed on the first roller component.

In another embodiment, the present invention is a method of monitoring an undercarriage comprising the steps of providing a roller assembly including a bushing and disposing a sensor on the roller assembly to sense a physical characteristic of the bushing.

DETAILED DESCRIPTION OF THE DRAWINGS

The present invention is described in one or more embodiments in the following description with reference to the Figures, in which like numerals represent the same or similar elements. While the invention is described in terms of the best mode for achieving the invention's objectives, it will be appreciated by those skilled in the art that it is intended to cover alternatives, modifications, and equivalents as may be included within the spirit and scope of the invention as defined by the appended claims and their equivalents as supported by the following disclosure and drawings.

Monitoring the operational state of an undercarriage internally is a more effective way to determine wear and prevent undercarriage damage than monitoring the external condition of an undercarriage. Internal monitoring of undercarriage wear allows deterioration of lubricant or bearings to be detected within a roller assembly before a roller is damaged. Early detection of lubricant problems and bearing wear through constant monitoring allows lubricant and bearings to be replaced or repaired before irreparable damage is done to a roller. Repairing or rebuilding a roller assembly is less expensive than replacing a roller, but repair of the roller assembly is available only before damage is done to the roller. Maintaining lubricant and bearings prevents damage to the roller assembly. Therefore, detecting lubricant problems and bearing wear earlier leads to less costly maintenance of an undercarriage.

In order to know when lubricant and bearings within a roller assembly need maintenance, an internal monitoring system is beneficial. An internal monitoring system of an undercarriage allows the present operational state inside the roller assembly to be monitored so that roller assembly parts can be repaired before the roller is damaged and needs to be replaced. Therefore, an internal monitoring system for roller assemblies is described herein.

Figure 1:
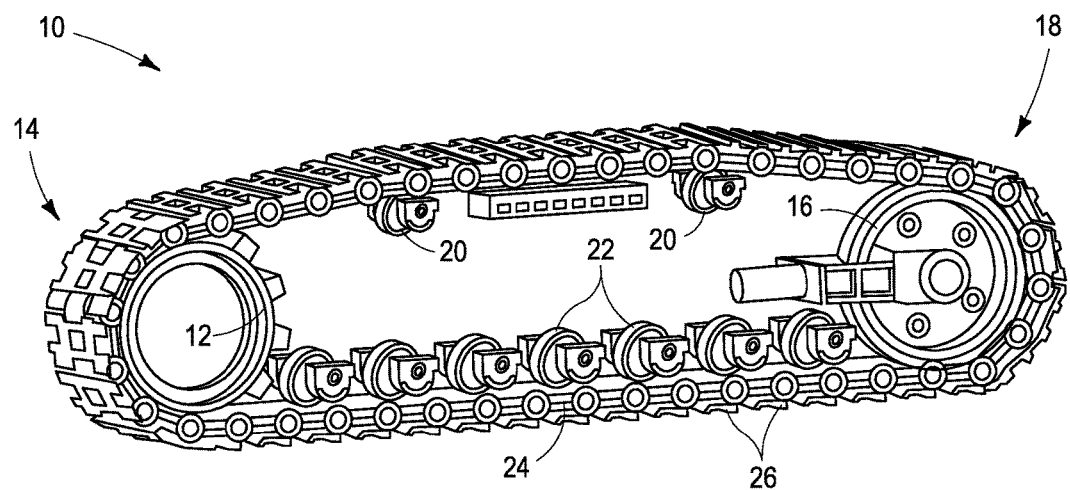
FIG. 1 illustrates a portion of a track undercarriage including rollers.

FIG. 1 illustrates a portion of a track undercarriage including rollers which are monitored with a monitoring device. The portion of undercarriage 10 shown in FIG. 1 is part of a track type undercarriage and can be incorporated into an undercarriage for many types of heavy equipment, such as a hydraulic and electric excavator, backhoe, shovel, drill, or other machine, including a tank. A complete undercarriage typically includes two track portions with one track portion disposed on each side of the complete undercarriage. Undercarriage 10 can be a different size or configuration in order to fit different types of heavy equipment for different industries or uses. Undercarriage 10 includes a sprocket 12 at rear 14 of undercarriage 10 and an idler 16 at front 18 of undercarriage 10. Undercarriage 10 includes a plurality of upper roller assemblies or upper rollers 20. Two upper rollers 20 are depicted in FIG. 1. Undercarriage 10 includes a plurality of lower roller assemblies or lower rollers 22. Seven lower rollers 22 are depicted in FIG. 1. However, undercarriage 10 can be designed with fewer or additional upper rollers 20 and lower rollers 22. Track 24 is made up of individual track shoes 26 linked together in a continuous chain. Track 24 is disposed around sprocket 12, idler 16, upper rollers 20, and lower rollers 22. Track 24 rotates in both the clockwise and counterclockwise directions around sprocket 12, idler 16, upper rollers 20, and lower rollers 22.

An undercarriage frame, not shown in FIG. 1, supports the upper structure of heavy equipment. The undercarriage frame includes a frame portion which fits within track 24 of undercarriage 10. The body of the excavator, backhoe, shovel, drill, or other equipment is coupled to the undercarriage frame. The undercarriage frame may include any style necessary to support the equipment, such as an H-style body, a square-style body, or other body style. The upper structure of the equipment is disposed on an undercarriage frame which is driven or mobilized by undercarriage 10. The portion of the undercarriage frame which fits within undercarriage 10 couples to or contacts idler 16, upper rollers 20, and lower rollers 22. Track 24 rotates around the undercarriage frame to mobilize undercarriage 10. The weight of the undercarriage frame and upper structure of the heavy equipment is supported by the plurality of rollers which roll as track 24 rotates to move undercarriage 10.

Undercarriage 10 withstands a significant amount of weight, stress, and wear under normal operating conditions. Over time, components of undercarriage 10 wear out and must be repaired or replaced. Rollers, such as idler 16, upper rollers 20, and lower rollers 22 each include bushings and lubricant which are internal to the rollers. The wear and damage caused by worn out bushings and inadequate lubrication is difficult to determine by visual or physical inspection of the rollers while the rollers are mounted to undercarriage 10. Therefore, an internal monitoring device is used to monitor the wear and operational state of the lubricant and bushing within each roller. A monitoring device including sensor or sensors allows a roller to be monitored constantly rather than while the equipment is running during daily operation. A monitoring device is disposed on or within each roller assembly on undercarriage 10. The monitored roller assemblies include idler 16, upper rollers 20, and lower rollers 22.

Figure 2:
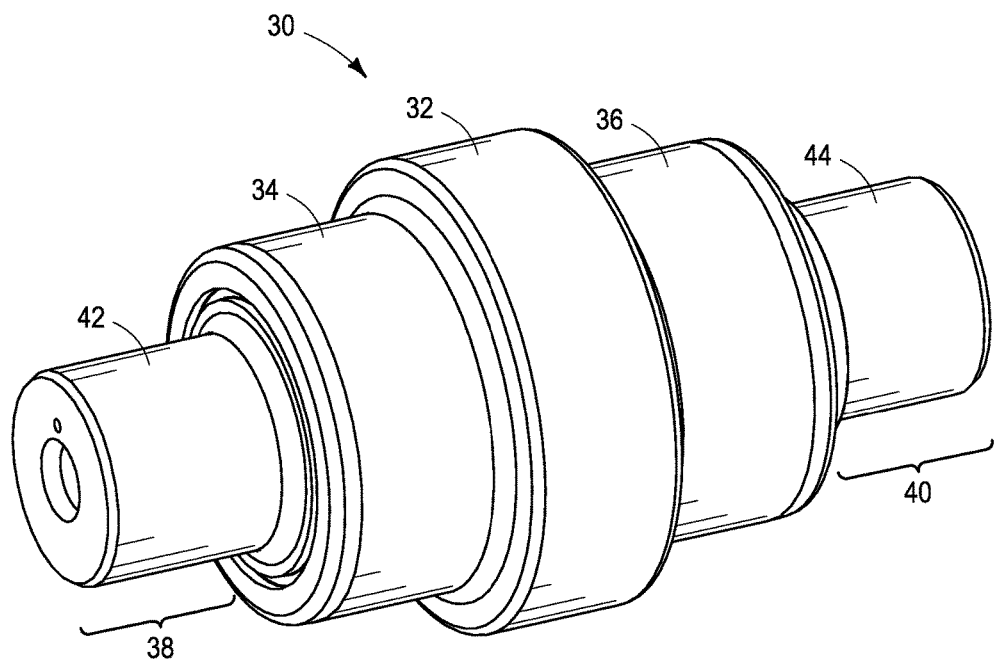
FIG. 2 illustrates a roller for a track undercarriage which can be monitored with a sensor.

FIG. 2 illustrates a roller which can be monitored with a monitoring device. Roller body 30 is a part of a roller assembly which facilitates the movement of track 24 around the undercarriage frame. Roller body 30 is an example of a roller with a solid roller body in which roller body 30 is one piece. Roller body 30 includes a single flange 32. In an alternative embodiment, roller body 30 includes dual or multiple flanges. In another embodiment, roller body 30 is configured to rotate around a shaft. Track 24 makes contact with roller body 30 at surfaces 34 and 36 adjacent to flange 32. Roller body 30 includes end 38 and end 40 opposite to end 38. Ends 38 and 40 of roller body 30 are each configured to fit within an end cap of a roller assembly. End 38 of roller body 30 includes surface 42, and end 40 includes surface 44. Roller body 30 can be metal, such as high strength steel, hardened steel, carbon steel, metal alloy, or other material. In one embodiment, roller body 30 is hardened steel. Roller body 30 is monitored with the monitoring device disposed within the roller assembly to detect wear within the roller assembly before roller body 30 is damaged.

Figure 3:
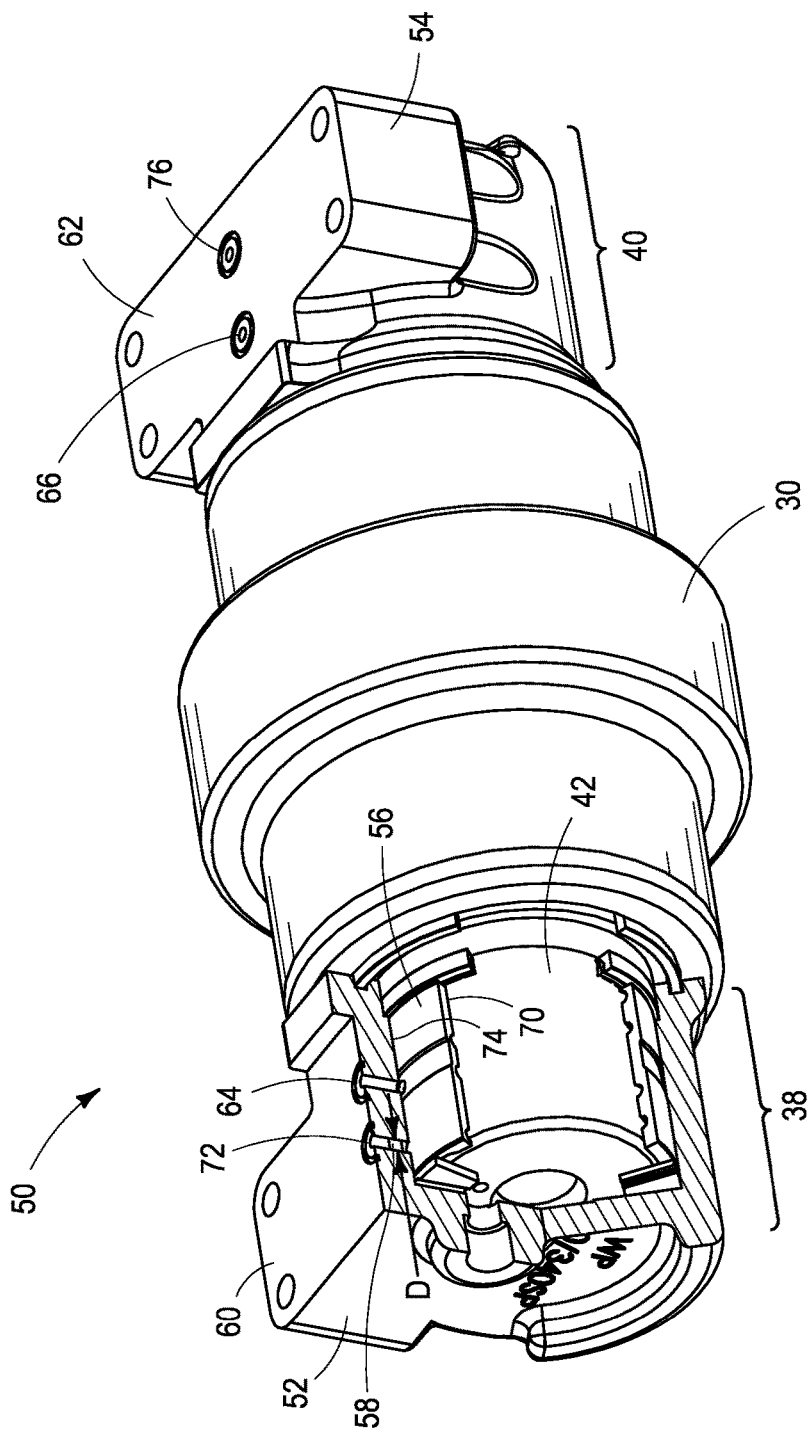
FIG. 3 illustrates a roller assembly including a monitoring device.

FIG. 3 illustrates roller assembly with a roller and sensors mounted within end caps. Roller assembly 50 includes roller body 30, end caps 52 and 54, bushings 56, and monitoring devices 58. A portion of roller assembly 50 is cut away in FIG. 3 to show internal components of roller assembly. Roller body 30 is partially disposed within and is rotationally coupled to end caps 52 and 54. End caps 52 and 54 have similar structures, and features described of end cap 52 or 54 apply to both end caps 52 and 54. End caps 52 and 54 constitute a housing for each of ends 38 and 40 of roller body 30. End caps 52 and 54 are rigidly attached to or mounted to the undercarriage frame and roller body 30 is mounted to the undercarriage frame by end caps 52 and 54. End caps 52 and 54 can be metal, including high strength steel, hardened steel, carbon steel, metal alloy, or other metal. End caps 52 and 54 include a plurality of openings or drilled holes for accommodating fasteners and other roller assembly components. Openings 64 is formed through surface 60 of end cap 52. Opening 66 is similar to opening 64 and is formed through surface 62 of end cap 54. Openings 64 and 66 in end caps 52 and 54, respectively, allow lubricant to flow into the inside of end caps 52 and 54 to lubricate bushings 56 and surfaces 42 and 44 at ends 38 and 40 of roller body 30.

Bushings 56 are disposed within end caps 52 and 54 of roller assembly 50. Bushing 56 constitutes a bearing disposed between end 38 of roller body 30 and end cap 52 to reduce the friction between roller body 30 and end cap 52. In one embodiment, bushing 56 is fixed within end cap 52. Roller body 30 rotates within end cap 52 and bushing 56. A bushing similar to bushing 56 is fixed within end cap 54 at the end 40 of roller body 30. Bushing 56 allows roller body 30 to turn or rotate within end caps 52 and 54 without damaging roller body 30 or end caps 52 and 54 by reducing friction between roller body 30 and end caps 52 and 54.

Bushings 56 include inner surface 70 which contacts surface 42 of roller body 30 at end 38 of roller body 30. A lubricant is disposed between surface 42 of roller and surface 70 of bushing 56 to reduce the friction between surface 42 of roller body 30 and inner surface 70 of bushing 56. The lubricant between roller body 30 and bushing 56 reduces the friction caused by roller body 30 rotating within end cap 54. In an automatic lubrication system, lubricant is regularly pumped through openings 64 and 66 into end caps 52 and 54 to lubricate bushing 56 and roller body 30 while undercarriage 10 is driving and roller body 30 is rotating. An opening is formed through bushing 56 to allow lubricant to reach inner surface 70 of bushing 56. In a self-contained lubrication system, lubricant is sealed inside the roller assembly. In either the automatic lubrication system or the self-contained lubrication system, the quantity and quality of lubrication between inner surface 70 of bushing 56 and surface 42 of roller body 30 is monitored while roller assembly 50 is mounted to the undercarriage frame using monitoring device 58. Monitoring device 58 can be incorporated into a lubrication system in order to monitor the lubrication and bushing wear within end cap 54. Alternatively, monitoring device 58 is separate from the lubrication system and can be incorporated into existing roller assemblies.

Opening 72 is formed completely through end cap 52 extending from surface 60 to an inner surface 74 of end cap 52. Monitoring device 58 is disposed within opening 72. Monitoring device 58 includes one or more sensors to measure one or more physical characteristics of bushing 56, roller body 30, and the lubricant. Opening 72 is formed with a diameter D appropriate to fit monitoring device 58. In one embodiment, diameter D of opening 72 is approximately 1.8 centimeters (cm), or 0.7 inches. In an alternative embodiment, opening 72 can be formed with a diameter greater than or less than 1.8 cm. Opening 72 is formed with a diameter large enough to accommodate monitoring device 58. In an alternative embodiment, additional openings are formed partially or completely through end cap 52 to accommodate additional components of monitoring device 58. Opening 72 is formed such that opening 72 does not degrade the strength and functionality of end cap 52. In an alternative embodiment, opening 72 is formed through a surface of end cap 52 other than surface 60.

Opening 76 is similar to opening 72 and is formed completely through end cap 54 extending from surface 62 to an inner surface of end cap 54 to monitor the bushing within end cap 54. A second monitoring device 58 is disposed within opening 76. Monitoring device 58 includes one or more sensors to measure one or more physical characteristics of bushing 56, roller body 30, and the lubricant. Opening 76 is formed with a diameter appropriate to fit monitoring device 58. In one embodiment, the diameter of opening 76 is approximately 1.8 centimeters (cm), or 0.7 inches. In an alternative embodiment, opening 76 can be formed with a diameter greater than or less than 1.8 cm. Opening 76 is formed with a diameter large enough to accommodate monitoring device 58. In an alternative embodiment, additional openings are formed partially or completely through end cap 54 to accommodate additional components of monitoring device 58. Opening 76 is formed such that opening 76 does not degrade the strength and functionality of end cap 52. In an alternative embodiment, opening 76 is formed through a surface of end cap 54 other than surface 62.

Figure 4:
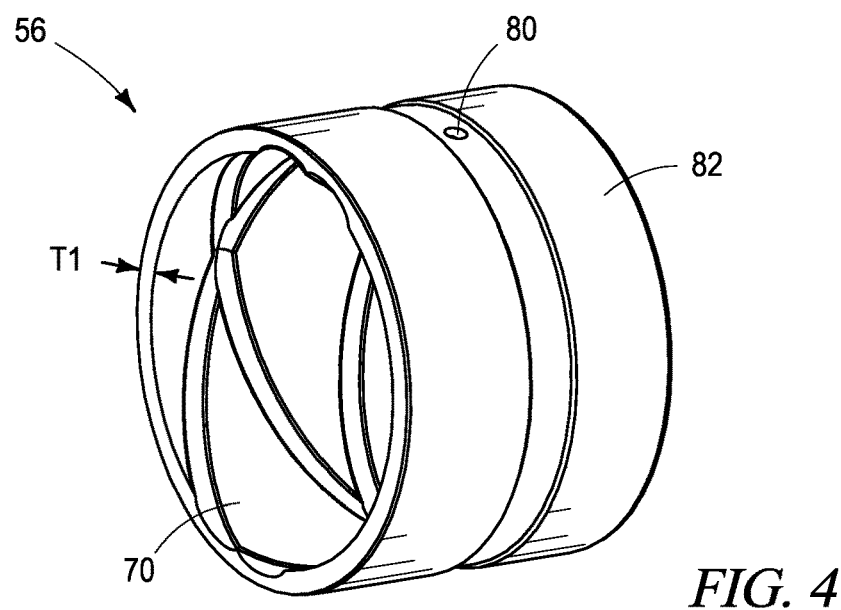
FIG. 4 illustrates a roller bearing which can be monitored with a monitoring device.

FIG. 4 illustrates a bushing which is monitored with a monitoring device. Bushing 56 may include opening 80 extending from outer surface 82 to inner surface 70 to facilitate lubricant flow. Bushing 56 can be metal, including copper, tin, zinc, nickel, iron, aluminum, or other metal or can be metal alloy such as copper and tin, known as bronze, copper and zinc, or other metal alloy. In one embodiment, bushing 56 is bronze, a nonferrous metal, and is a softer metal than roller body 30 and end cap 52. When bushing 56 is new, bushing 56 has a thickness T1 which is the thickness of a new bushing without wear. Bushing 56 is monitored by monitoring device 58 while bushing is disposed within roller assembly 50 which is mounted within undercarriage 10.

Figure 5:
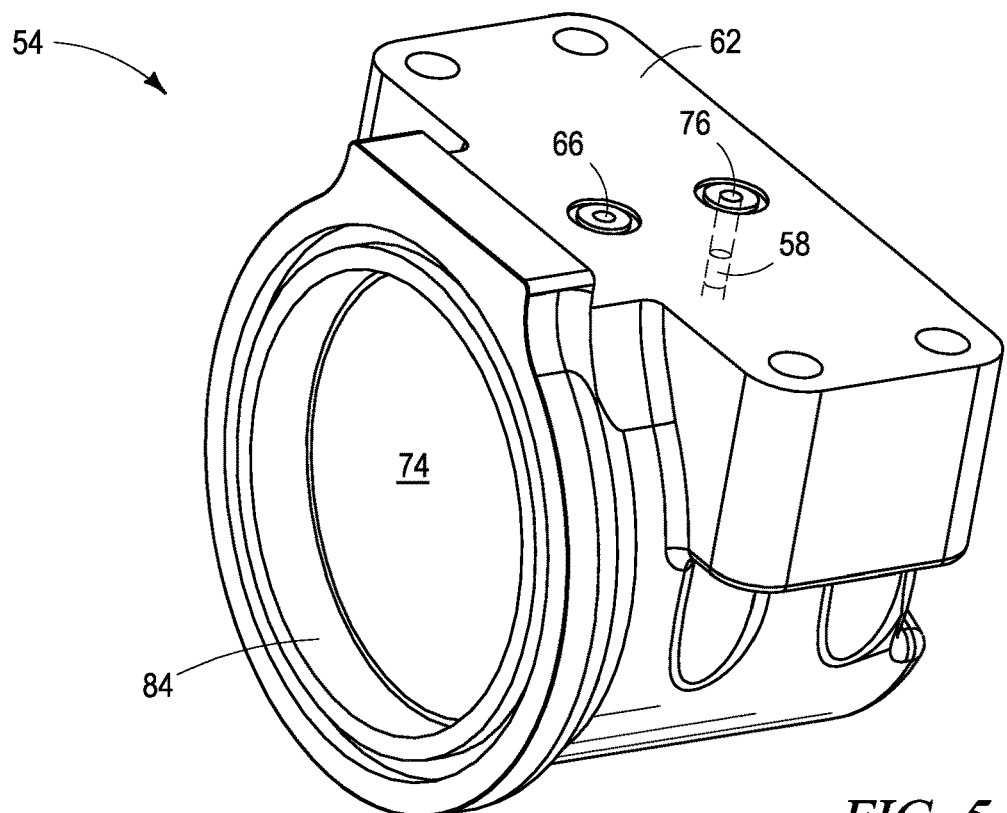
FIG. 5 illustrates a roller assembly end cap including a monitoring device disposed within the end cap.

FIG. 5 illustrates an end cap of a roller assembly including a monitoring device disposed within the end cap. End cap 54 is part of roller assembly 50 and accommodates a roller body 30. Opening 84 in end cap 54 is formed partially or completely through end cap 54 to accommodate roller body 30. Additional openings are formed through end cap 54 to accommodate fasteners and other functions. Opening 66, for example, is formed completely through surface 62 of end cap 54 and acts as a lubricant delivery opening. Opening 76 is formed completely through surface 62 of end cap 54. Opening 76 provides a location for monitoring device 58 to be housed within end cap 54. In one embodiment, monitoring device 58 is disposed completely or partially within opening 76. In an alternative embodiment, additional openings are formed partially or completely through end cap 52 and monitoring device 58 includes a sensor disposed within a first opening and an additional component, such as a magnet, disposed in a second opening. Monitoring device 58 is further coupled to wiring and circuitry to enable data from monitoring device 58 to be stored and transferred. The wiring and circuitry may be disposed with opening 76 or within other openings in end cap 54 or may be mounted to end cap 54 or roller assembly 50.

Returning to FIG. 3, end caps 52 and 54 constitute the parts of roller assembly 50 which couple to roller body 30. Each of end caps 52 and 54 include monitoring device 58 disposed within the end caps which act as a housing or a mounting point for monitoring device 58. A monitoring device 58 is placed within each of openings 72 and 76 in close proximity to bushings 56 or in contact with bushings 56. Monitoring device 58 may include one sensor or multiple sensors. In one embodiment, multiple sensors are accommodated within monitoring device 58 which is formed into one unit and fits within openings 72 and 76. In an alternative embodiment, additional openings similar to openings 72 and 76 are formed completely or partially through end caps 52 and 54 to accommodate multiple monitoring devices 58 or multiple sensors or components of monitoring device 58.

Monitoring device 58 monitors a physical characteristic of roller assembly 50 in order to detect a problem within roller assembly 50. Monitoring device 58 measures temperature of roller assembly 50 and thickness of bushing 56, determines the presence or absence of lubricant within roller assembly 50, and determines if bushing 56 has been worn completely away. Monitoring device 58 includes a sensor such as a Hall effect sensor, temperature sensor, particulate sensor, viscosity sensor, depth sensor, or other type of sensor. In one embodiment, monitoring device 58 measures a temperature at a surface of bushing 56 or a temperature within end cap 52. In an alternative embodiment, monitoring device 58 measures thickness of bushing 56 using a magnet and a Hall effect sensor. In another embodiment, monitoring device 58 includes both a temperature sensor and a Hall effect sensor with a magnet. The temperature sensor, Hall effect sensor, and magnet of monitoring device 58 fit within openings 72 and 76 in end caps 52 and 54 respectively. End caps 52 and 54 can be configured with additional openings or ports to accommodate additional sensors and other components of monitoring device 58. In one embodiment, a temperature sensor is disposed in a first opening and a Hall effect sensor is disposed in a second opening. In another embodiment, a Hall effect sensor is disposed in one opening and a magnet is disposed in a second opening such that the sensor is disposed between bushing 56 and the magnet.

In one embodiment of monitoring device 58, a temperature sensor is used to determine the lubricant status within roller assembly 50. Increased temperature within roller assembly 50 is one indicator of inadequate lubrication of bushing 56. A temperature sensor is disposed within or mounted to roller assembly 50 to measure the temperature of roller assembly 50 within end caps 52 and 54. When lubrication runs low or runs out, the friction between surface 42 of roller body 30 and inner surface 70 of bushing 56 increases. Without lubricant, surface 42 of roller body 30 directly contacts inner surface 70 of bushing 56. Roller body 30 and bushing 56 are metal, resulting in metal on metal contact. The increased friction between roller body 30 and bushing 56 results in increased temperature at roller body 30 and bushing 56 within end caps 52 and 54. The change in temperature caused by reduced lubrication or a lack of lubrication is detected or sensed by the temperature sensor of monitoring device 58. The temperature sensor may include a contact sensor, such as a thermocouple, thermistor, resistance temperature detector (RTD), or a non-contact temperature sensor, such as an infrared heat sensor. In an alternative embodiment, monitoring device 58 measures the viscosity of the lubricant to determine the quality of lubrication within roller assembly 50. In another embodiment, monitoring device 58 includes a particulate sensor to determine the quality of lubrication and amount of metal particulates within roller assembly 50.

Figure 6:
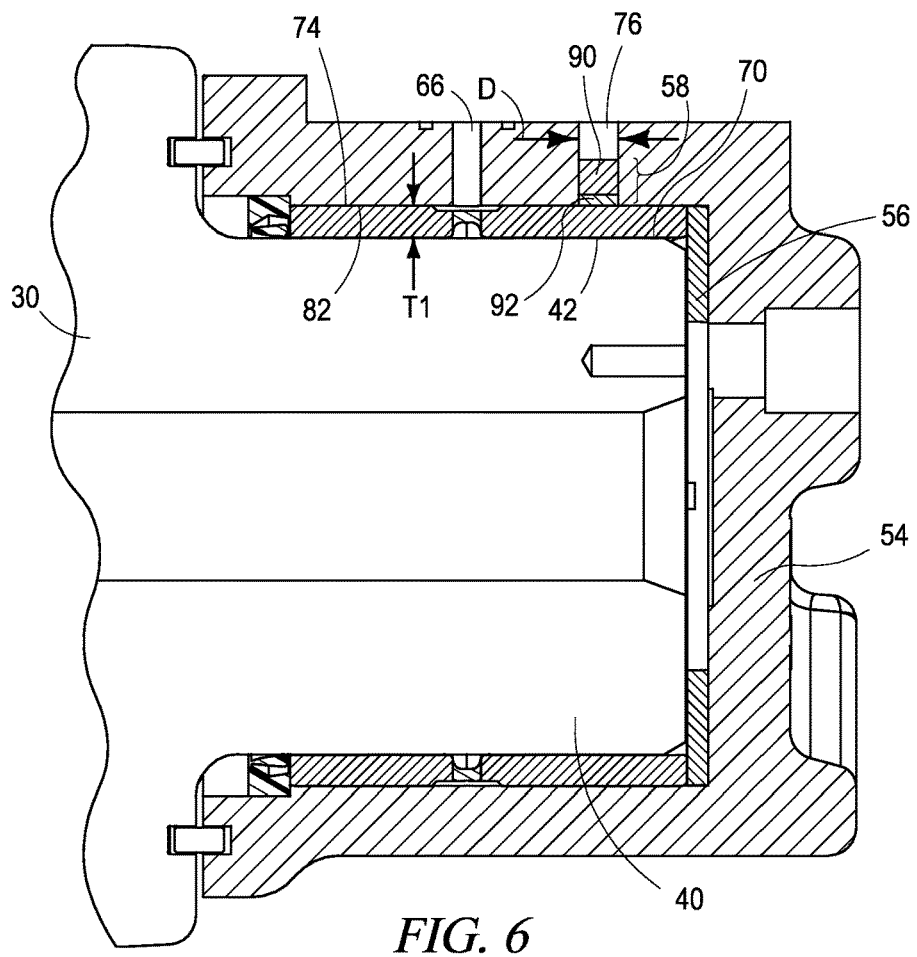
FIG. 6 illustrates a cross section of a roller assembly including a roller, a bearing, and a monitoring device.

FIG. 6 illustrates a cross section of a roller assembly including a roller, a bearing, and a monitoring device. End cap 54 includes bushing 56 fixed on inner surface 74 of end cap 54. In a fixed bushing design, roller body 30 rotates within bushing 56 and end cap 52. Opening 76 or a plurality of openings 76 is formed through end cap 52 to provide a housing for monitoring device 58. Monitoring device 58 is disposed within opening 76 or various components of monitoring device 58 are disposed in multiple openings. Monitoring device 58 includes at least one sensor, such as a Hall effect sensor, temperature sensor, particulate sensor, viscosity sensor, depth sensor, or other type of sensor.

In one embodiment of monitoring device 58, Hall effect sensor 92 is used to measure a thickness of bushing 56 to determine the amount of wear on bushing 56. Monitoring device 58 includes magnet 90 and Hall effect sensor 92. Hall effect sensor 92 is disposed within opening 76. In one embodiment, magnet 90 is disposed within opening 76 over Hall effect sensor 92 such that Hall effect sensor 92 is disposed between magnet 90 and bushing 56. Bushing 56 is disposed between Hall effect sensor 92 and roller body 30. A Hall effect sensor includes a transducer which responds to a magnetic field by producing a voltage. Hall effect sensor 92 responds to the magnetic field between magnet 90 and roller body 30. In roller assembly 50, bushing 56 is typically bronze, a similar copper alloy, or other alloy or metal. Bronze is a non-ferrous metal and is unaffected by a magnet. Roller body 30 is typically hardened steel, or other type of steel or metal. Steel is a ferrous material and is attracted to a magnet. Therefore, roller body 30 responds to magnet 90 and bushing 56 is unaffected by magnet 90. The magnetic field between magnet 90 and roller body 30 passes through the non-ferrous bushing 56 in between magnet 90 and roller body 30. The distance between roller body 30 and magnet 90 determines a magnetic field at Hall effect sensor 92 which is converted into a voltage by Hall effect sensor 92. The thickness of bushing 56 determines the distance between roller body 30 and magnet 90 because bushing 56 separates roller body 30 from end cap 54 where magnet 90 is located. The magnetic field between roller body 30 and magnet 90 changes when bushing 56 wears down and becomes thinner and roller body 30 moves closer to or farther away from magnet 90. Therefore, monitoring device with magnet 90 and Hall effect sensor 92 detects the amount of wear on bushing 56 by indirectly measuring the thickness of bushing 56.

In an alternative embodiment of monitoring device 58, Hall effect sensor 92 is disposed on one side of bushing 56 and magnet 90 is disposed on a side of bushing 56 opposite the side where Hall effect sensor 92 is disposed. Bushing 56 is disposed between magnet 90 and Hall effect sensor 92. The magnetic field of magnet 90 passes through bushing 56 and is sensed by Hall effect sensor 92. For example, Hall effect sensor 92 is disposed within opening 76 and magnet is not disposed within opening 76, but is disposed in an opening formed through end 40 of roller body 30 or is disposed within bushing 56. As the thickness of bushing 56 changes, the position of Hall effect sensor 92 changes with respect to magnet 90. As Hall effect sensor 92 moves closer to or is positioned closer to magnet 90, the magnetic field increases and the voltage produced by Hall effect sensor 92 increases. As Hall effect sensor 92 moves farther from or is positioned farther away from magnet 90, the magnetic field decreases and the voltage produced by Hall effect sensor 92 decreases. Therefore, monitoring device with magnet 90 and Hall effect sensor 92 detects the amount of wear on bushing 56 by directly measuring the thickness of bushing 56.

Figure 7:
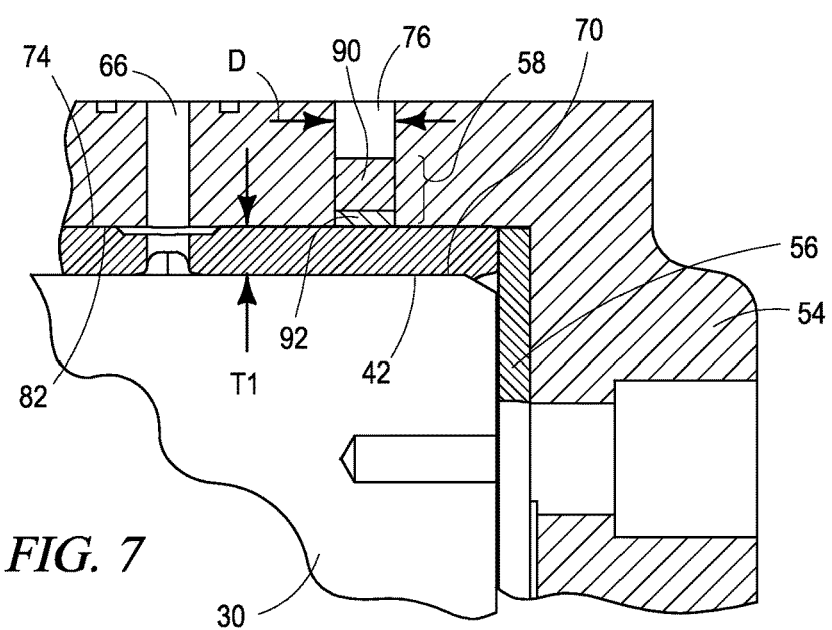
FIG. 7 illustrates further detail of a cross section of a roller, a bearing, and a monitoring device.

FIG. 7 shows further detail of the cross section in FIG. 6 of a roller, a bearing, and a monitoring device. Roller body 30 is disposed in close proximity to or in contact with bushing 56. A thin layer of lubrication, if present, separates surface 42 of roller body 30 and inner surface 70 of bushing 56. During normal operation, roller body 30 rotates smoothly within bushing 56 along inner surface 70 of bushing 56. A thickness T1 of bushing 56 is the thickness of a new, unworn, and undamaged bushing. In one embodiment, monitoring device 58 is disposed on outer surface 82 of bushing 56 within opening 76 in end cap 54. In another embodiment, Hall effect sensor 92 is disposed in opening 76 and magnet 90 is disposed in an additional opening adjacent to opening 76 in end cap 54. Hall effect sensor 92 produces a voltage which correlates to bushing thickness T1 or the distance between surface 42 of roller body 30 and magnet 90. In an alternative embodiment, magnet 90 is disposed on one side of bushing 56 and Hall effect sensor 92 is disposed on an opposite side of bushing 56. Hall effect sensor 92 produces a voltage which correlates to bushing thickness T1 or to the distance between Hall effect sensor 92 and magnet 90. When magnet 90 is disposed within or on roller body 30, Hall effect sensor 92 produces a voltage which correlates to the distance between Hall effect sensor 92 and roller body 30 where magnet 90 is located. In each embodiment, monitoring device 58 functions even while roller body 30 is moving or rotating. Monitoring device 58 produces output data which indicates the bushing thickness thereby reporting an operational state of bushing 56 in real-time.

Figure 8:
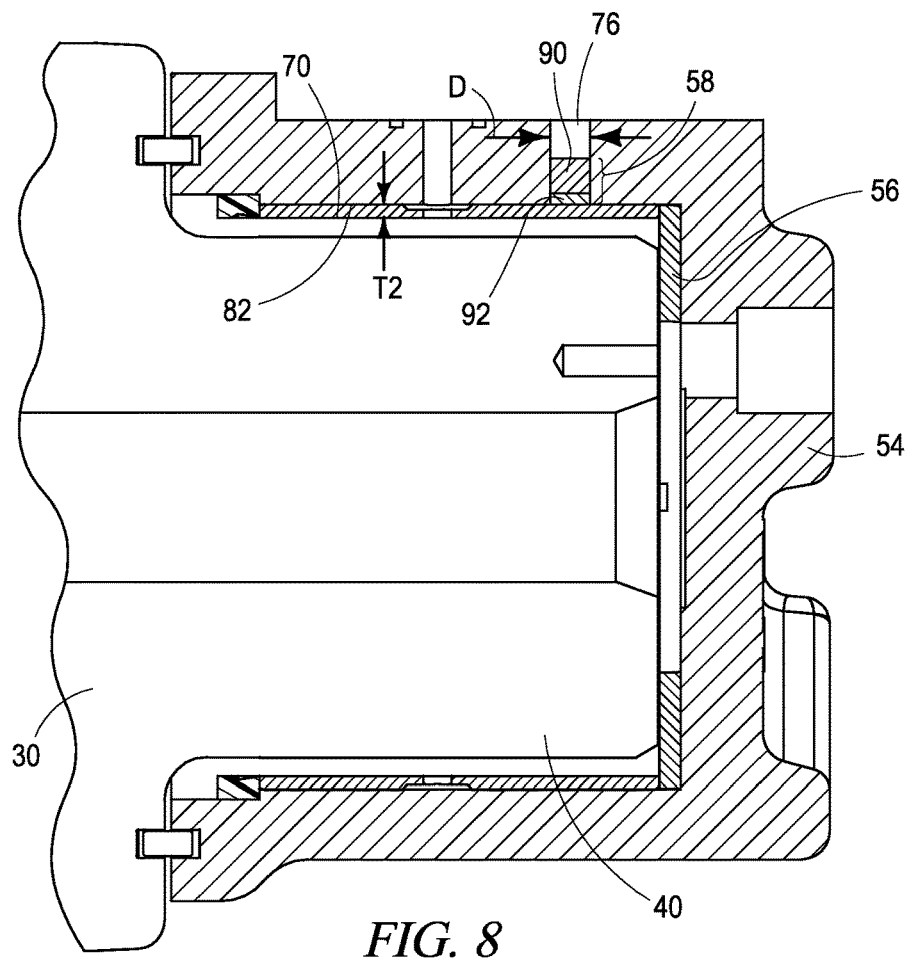
FIG. 8 illustrates a cross section of a roller assembly including a roller, a bearing showing wear, and a monitoring device.

FIG. 8 shows a cross section of a roller assembly including a roller, a bearing showing wear, and a monitoring device. Roller body 30 is disposed within end cap 54 and bushing 56. Bushing 56 is fixed within end cap 54. Roller body 30 spins or rotates within end cap 54 and bushing 56. Roller body 30 includes surface 42 which contacts inner surface 70 of bushing 56 as roller body 30 spins. Under ideal operating conditions, lubricant is disposed within end cap between surface 42 of roller body 30 and inner surface 70 of bushing 56. Without adequate lubrication, roller body 30 grinds against bushing 56 with increased friction causing increased heat within end cap 54 and causing bushing 56 to be worn away. Bushing 56 is typically bronze or a softer metal than roller body 30. Roller body 30 rubs bushing 56, wearing down bushing 56 at inner surface 70 as roller body 30 spins without lubrication. When bushing 56 is worn down by roller body 30, bushing 56 becomes thinner. Thickness T2 indicates the reduced thickness of bushing 56 as a result of wear on bushing 56 by roller body 30.

Figure 9:
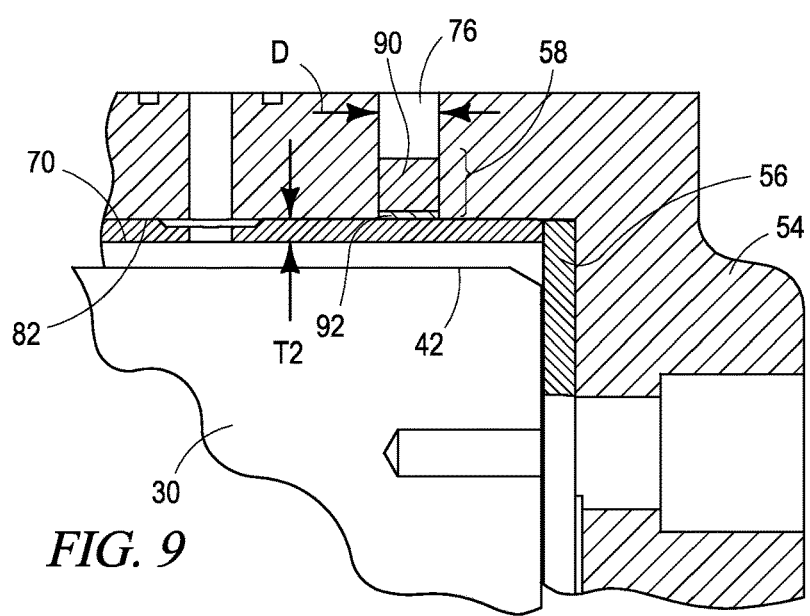
FIG. 9 illustrates further detail of a cross section of a roller assembly including a roller, a bearing showing wear, and a monitoring device.

FIG. 9 shows further detail of the cross section in FIG. 8 of a roller assembly including a roller, a bearing showing wear, and a monitoring device. Without adequate lubrication or simply over time, surface 42 of roller body 30 wears on inner surface 70 of bushing 56. Roller body 30 presses against inner surface 70 of bushing 56, so when bushing 56 is thinned, roller body 30 no longer fits properly within bushing 56. Roller body 30 may move closer to or farther away from inner surface 74 of end cap 54.

In one embodiment, when bushing thickness T1 is reduced to thickness T2, roller body 30 changes position relative to inner surface 74 of end cap 54 and to magnet 90. The magnetic field at Hall effect sensor 92 increases as roller body 30 moves closer to magnet 90, and decreases as roller body 30 moves farther from magnet 90. Hall effect sensor 92 produces a higher or lower output voltage which correlates to the position of roller body 30 due to the reduced thickness of bushing 56. The magnetic field at Hall effect sensor 92 changes as bushing 56 changes thickness compared to bushing thickness T1. The difference in the Hall effect between new bushing 56 and worn bushing 56 correlates to the difference between thickness T1 and T2. An output voltage of Hall effect sensor 92 is thereby used to monitor the thickness of bushing 56.

In an alternative embodiment, magnet 90 is disposed on one side of bushing 56 and Hall effect sensor 92 is disposed on an opposite side of bushing 56. Hall effect sensor 92 produces a voltage which correlates to the distance between Hall effect sensor 92 and magnet 90 which correlates to the thickness of bushing 56. When bushing 56 wears down and becomes thinner, the distance between Hall effect sensor 92 and magnet 90 increases or decreases depending on where each of the components are mounted on roller assembly 50. When magnet 90 is disposed on or within roller body 30 and Hall effect sensor 92 is disposed within end cap 54, the distance between Hall effect sensor 92 and magnet 90 changes as bushing 56 thins. As the distance between Hall effect sensor 92 and magnet 90 changes, the magnetic field at Hall effect sensor 92 changes and Hall effect sensor 92 produces a change in voltage. Alternatively, Hall effect sensor 92 or magnet 90 is disposed on bushing 56. In each embodiment, the output voltage of Hall effect sensor 92 indicates the change in bushing thickness. In another alternative embodiment, monitoring device 58 includes a depth sensor to determine the thickness bushing 56.

The temperature sensor and Hall effect sensor 92 within monitoring device 58 produce output signals or output data. The output from monitoring device 58 is transferred to an external receiving device which processes the signals or data output. A transmitter or connection port is used to transfer signal or data output from monitoring device 58 to an external receiving device, such as a computer. The transmitted data can then be uploaded to a computer or other device which processes the data. Data from monitoring device 58 is used to monitor the operational condition of roller assembly 50. As monitoring device 58 measures, for example, the temperature within the end caps 52 and 54 and thickness of bushing 56, the monitoring device produces output signals or data which is transferred through a wireless transmitter to a computer. Alternatively, the output data is accessed through a port which connects to monitoring device 58. The output data is processed and is used to determine if roller assembly 50 is operating at the proper temperature and bushing thickness. If the data indicates a problem with roller assembly 50, the problem can be recognized immediately. For example, if the temperature data indicates that the roller assembly has reached an abnormally high temperature, a manual or automatic alarm is triggered. For example, a person can monitor the data and call the equipment operator when a roller assembly within the equipment reaches a certain temperature or becomes too hot. Alternatively, the computer includes an algorithm that automatically triggers a warning indicator to the equipment operator when a roller assembly reaches a certain temperature. Similarly, if the Hall effect reaches a certain voltage indicating bushing wear, a manual or automatic alarm is triggered. Therefore, monitoring device 58 allows real-time feedback about the temperature and bushing thickness for roller assembly 50.

Real-time monitoring of roller assembly 50 allows problems with lubricant and bushings to be addressed earlier and before damage to roller assembly 50 occurs. An operator is alerted when lubricant runs dry and stop the equipment before roller body 30 quickly wears through bushing 56 causing premature failure of roller assembly. Lubricant can simply be replaced or a lubrication system repaired, rather than replacing an entire damaged roller assembly. Bushing wear can be monitored regularly and bushings 56 can be replaced before bushings 56 are worn completely through and roller body 30 begins to grind into end caps 52 and 54. Bushings can be replaced before damage to roller assembly 50 is too substantial to be repaired. Monitoring device 58 thereby provides a preventative monitoring and maintenance tool that reduces maintenance costs in track undercarriages by detecting roller problems early and preventing premature roller failure.

Figure 10:
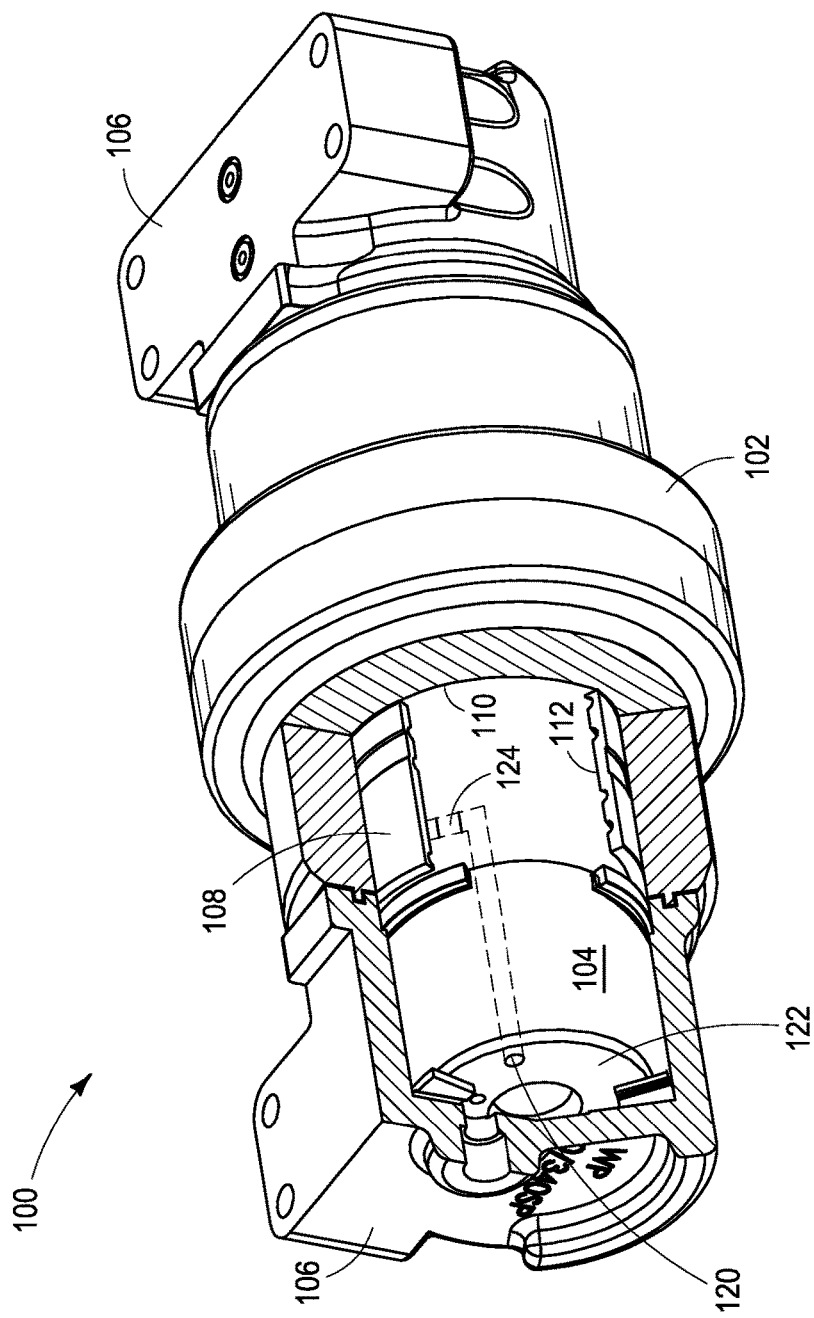
FIG. 10 illustrates an alternative embodiment of a roller assembly including a monitoring device disposed within the shaft.

FIG. 10 illustrates an alternative embodiment of a roller assembly including a monitoring device disposed within the shaft. A portion of roller assembly 100 is cut away in FIG. 10 to show internal components of roller assembly. Roller assembly 100 includes roller body 102, shaft 104, end caps 106, and bushings 108. Roller body 102 rotates around shaft 104. Bushings 108 are pressed into roller body 102 such that bushings 108 are fixed within roller body 102. Bushings 108 are rigidly affixed to inner surface 110 of roller body 102. Roller body 102 and bushings 108 rotate together around shaft 104, and therefore, are dynamic with respect to shaft 104. Roller body 102 can be metal, such as high strength steel, hardened steel, carbon steel, metal alloy, or other material. In one embodiment, roller body 102 is hardened steel. Roller body 102 is monitored with the monitoring device disposed within roller assembly 100 to detect wear within roller assembly 100 before roller body 102 is damaged. Roller body 102 rotates around fixed shaft 104. Shaft 104 is fixed within end caps 106. End caps 106 are rigidly attached to or mounted to the undercarriage frame and shaft 104 is mounted to the undercarriage frame by end caps 106. End caps 106 can be metal, including high strength steel, hardened steel, carbon steel, metal alloy, or other material.

Bushings 108 are disposed within roller assembly 100 to reduce the friction between roller body 102 and shaft 104. Bushing 108 allows roller body 102 to turn or rotate around shaft 104 without damaging roller body 102, bushings 108, or shaft 104. Bushings 108 includes inner surface 112 which contacts shaft 104. Bushing 108 can be metal, including copper, tin, zinc, nickel, iron, aluminum, or other metal or can be metal alloy such as copper and tin, known as bronze, copper and zinc, or other metal alloy. In one embodiment, bushing 108 is bronze, a nonferrous metal, and is a softer metal than roller body 102 and shaft 104. A lubricant is disposed between shaft 104 and surface 112 of bushing 108 to reduce the friction between shaft 104 and surface 112 of bushing 108. In a self-contained lubrication system, lubricant is sealed inside roller assembly 100.

Openings 120 are formed partially through each end 122 of shaft 104. Openings 120 are formed parallel to the length of shaft 104 at a depth sufficient to overlap bushing 108. Openings 120 include a portion that is oriented outwards toward a surface of shaft 104. Openings 120 thereby reach a surface of shaft 104 at a portion of shaft 104 near bushings 108. Alternatively, openings 120 do not reach another surface of shaft 104, but are formed through surface 122 of shaft 104 extending partially though shaft 104. Openings 120 may include a portion parallel to the length of shaft 104 formed completely through shaft 104.

Monitoring device 124 is disposed within opening 120. Monitoring device 124 includes one or more sensors to measure one or more physical characteristics of bushing 108, shaft 104, roller body 102, and the lubricant. Opening 120 is formed with a diameter appropriate to fit monitoring device 124. In one embodiment, the diameter of opening 120 is approximately 1.8 centimeters (cm), or 0.7 inches. In an alternative embodiment, opening 120 can be formed with a diameter greater than or less than 1.8 cm. Opening 120 is formed with a diameter large enough to accommodate monitoring device 124. Opening 120 is formed such that opening 120 does not degrade the strength and functionality of shaft 104.

A monitoring device 124 is placed within each of openings 120 in close proximity to bushings 108. Monitoring device 124 may include one sensor or multiple sensors. In one embodiment, multiple sensors are accommodated within monitoring device 124 which is formed into one unit and fits within openings 120. In an alternative embodiment, additional openings similar to openings 120 are formed through shaft 104 to accommodate multiple monitoring devices 124 or multiple sensors or components of monitoring device 124. In another embodiment, components of monitoring device 124 are disposed on or within bushing 108, roller body 102, or end caps 106. Monitoring device 124 can be incorporated into a lubrication system in order to monitor the lubrication within roller assembly 100. Alternatively, monitoring device 124 is separate from the lubrication system and can be incorporated into existing roller assemblies.

Monitoring device 124 monitors a physical characteristic of roller assembly 100 in order to detect a problem within roller assembly 100. Monitoring device 124 measures temperature of roller assembly 100 and thickness of bushing 108, determines the presence or absence of lubricant within roller assembly 100, and determines if bushing 108 has been worn completely away. Monitoring device 124 includes a sensor such as a Hall effect sensor, temperature sensor, particulate sensor, viscosity sensor, depth sensor, or other type of sensor. In one embodiment, monitoring device 124 measures a temperature at a surface of bushing 108 or a temperature within shaft 104. In an alternative embodiment, monitoring device 124 measures thickness of bushing 108 using a magnet and a Hall effect sensor. In another embodiment, monitoring device 124 includes both a temperature sensor and a Hall effect sensor with a magnet. The temperature sensor, Hall effect sensor, and magnet of monitoring device 124 fit within openings 120 in each end 122 of shaft 104, respectively. Alternatively, shaft 104, roller body 102, and bushing 108 are configured with additional openings or ports to accommodate additional sensors and other components of monitoring device 124.

In one embodiment of monitoring device 124, a temperature sensor is used to determine the lubricant status within roller assembly 100. Increased temperature within roller assembly 100 is one indicator of inadequate lubrication of bushing 108. A temperature sensor is disposed within or mounted to roller assembly 100 to measure the temperature of roller assembly 100 within roller body 102. When lubrication runs low or runs out, the friction between shaft 104 and inner surface 112 of bushing 108 increases. Without lubricant, shaft 104 directly contacts inner surface 112 of bushing 108. Shaft 104 and bushing 108 are metal, resulting in metal on metal contact. The increased friction between shaft 104 and bushing 108 results in increased temperature at shaft 104 and bushing 108 within roller assembly 100. The change in temperature caused by reduced lubrication or a lack of lubrication is detected by the temperature sensor of monitoring device 124. The temperature sensor may include a contact sensor, such as a thermocouple, thermistor, resistance temperature detector (RTD), or a non-contact temperature sensor, such as an infrared heat sensor. In an alternative embodiment, monitoring device 124 measures the viscosity of the lubricant to determine the quality of lubrication within roller assembly 100. In another embodiment, monitoring device 124 includes a particulate sensor to determine the quality of lubrication and amount of metal particulates within roller assembly 100.

In one embodiment of monitoring device 124, Hall effect sensor 92 is used to measure a thickness of bushing 108 to determine the amount of wear on bushing 108. Monitoring device 124 includes magnet 90 and Hall effect sensor 92. Hall effect sensor 92 is disposed within opening 120. In one embodiment, magnet 90 is disposed within opening 120 over Hall effect sensor 92 such that Hall effect sensor 92 is disposed between magnet 90 and bushing 108. Bushing 108 is disposed between Hall effect sensor 92 and roller body 102. The magnetic field between magnet 90 and roller body 102 passes through the non-ferrous bushing 108 in between magnet 90 and roller body 102. The distance between roller body 102 and magnet 90 determines a magnetic field at Hall effect sensor 92 which is converted into a voltage by Hall effect sensor 92. The thickness of bushing 108 determines the distance between roller body 102 and magnet 90 because bushing 108 separates roller body 102 from shaft 104 where magnet 90 is located. The magnetic field between roller body 102 and magnet 90 changes when bushing 108 wears down and becomes thinner and roller body 102 moves closer to or farther away from magnet 90. Therefore, monitoring device with magnet 90 and Hall effect sensor 92 detects the amount of wear on bushing 108 by indirectly measuring the thickness of bushing 108.

In an alternative embodiment of monitoring device 124, Hall effect sensor 92 is disposed on one side of bushing 108 and magnet 90 is disposed on a side of bushing 108 opposite the side where Hall effect sensor 92 is disposed. Bushing 108 is disposed between magnet 90 and Hall effect sensor 92. The magnetic field of magnet 90 passes through bushing 108 and is sensed by Hall effect sensor 92. For example, Hall effect sensor 92 is disposed within opening 120 and magnet is not disposed within opening 120, but is disposed in an opening formed through roller body 102 or is disposed on or within bushing 108. As the thickness of bushing 108 changes, the position of Hall effect sensor 92 changes with respect to magnet 90. As Hall effect sensor 92 moves closer to or is positioned closer to magnet 90, the magnetic field increases and the voltage produced by Hall effect sensor 92 increases. As Hall effect sensor 92 moves farther from or is positioned farther away from magnet 90, the magnetic field decreases and the voltage produced by Hall effect sensor 92 decreases. Therefore, monitoring device with magnet 90 and Hall effect sensor 92 detects the amount of wear on bushing 108 by directly measuring the thickness of bushing 108. In each embodiment, monitoring device 124 functions even while roller body 102 is moving or rotating. Monitoring device 124 produces output data which indicates the bushing thickness thereby reporting an operational state of bushing 108 in real-time.

The temperature sensor and Hall effect sensor 92 within monitoring device 124 produce output signals or output data. The output from monitoring device 124 is transferred to an external receiving device which processes the signals or data output. A transmitter or connection port is used to transfer signal or data output from monitoring device 124 to an external receiving device, such as a computer. The transmitted data can then be uploaded to a computer or other device which processes the data. Data from monitoring device 124 is used to monitor the operational condition of roller assembly 100 while roller assembly 100 is in use. Real-time monitoring of roller assembly 100 allows problems with lubricant and bushings to be addressed earlier and before damage to roller assembly 100 occurs.

Real-time monitoring of roller assembly 100 allows problems with lubricant and bushings to be addressed earlier and before damage to roller assembly 100 occurs. An operator is alerted when lubricant runs dry and stop the equipment before roller body 102 quickly wears through bushing 108 causing premature failure of roller assembly. Lubricant can simply be replaced or a lubrication system repaired, rather than replacing an entire damaged roller assembly. Bushing wear can be monitored regularly and bushings 108 can be replaced before bushings 108 are worn completely through and roller body 102 begins to grind into shaft 104. Bushings can be replaced before damage to roller assembly 100 is too substantial to be repaired. Monitoring device 124 thereby provides a preventative monitoring and maintenance tool that reduces maintenance costs in track undercarriages by detecting roller problems early and preventing premature roller failure.

Figure 11:
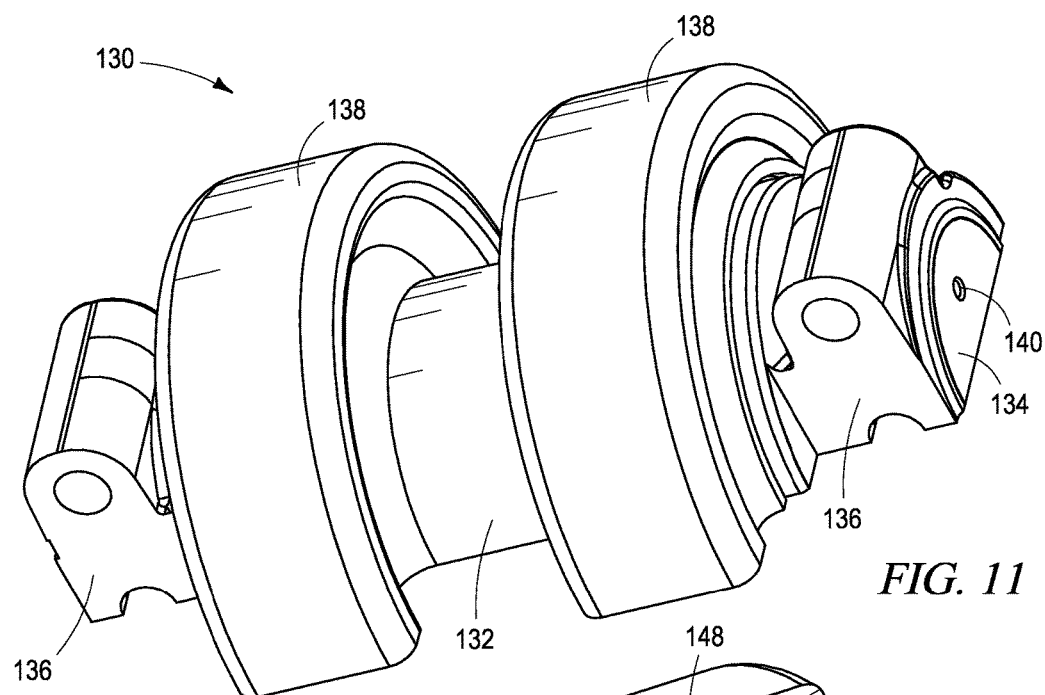
FIG. 11 illustrates an alternative embodiment of a roller assembly with dual flanges and including a monitoring device.

FIG. 11 shows a partial view of an alternative embodiment of a roller assembly with dual flanges and including a monitoring device. Roller assembly 130 includes roller body 132, shaft 134, end caps 136, and bushings. Roller body 132 includes dual flanges 138. Roller body 132 rotates around shaft 134. Roller body 132 can be metal, such as high strength steel, hardened steel, carbon steel, or other metal. In one embodiment, roller body 132 is hardened steel. Roller body 132 is monitored with the monitoring device disposed within the roller assembly to detect wear within the roller assembly before roller body 132 is damaged. Roller body 132 rotates around fixed shaft 134. Shaft 134 is fixed within end caps 136. End caps 136 are rigidly attached to or mounted to the undercarriage frame and roller body 132 is mounted to the undercarriage frame by end caps 136. End caps 136 can be metal, including high strength steel, hardened steel, carbon steel, or other metal. Opening 140 is formed partially through shaft 134 to provide a mounting point for a monitoring device.

Figure 12:
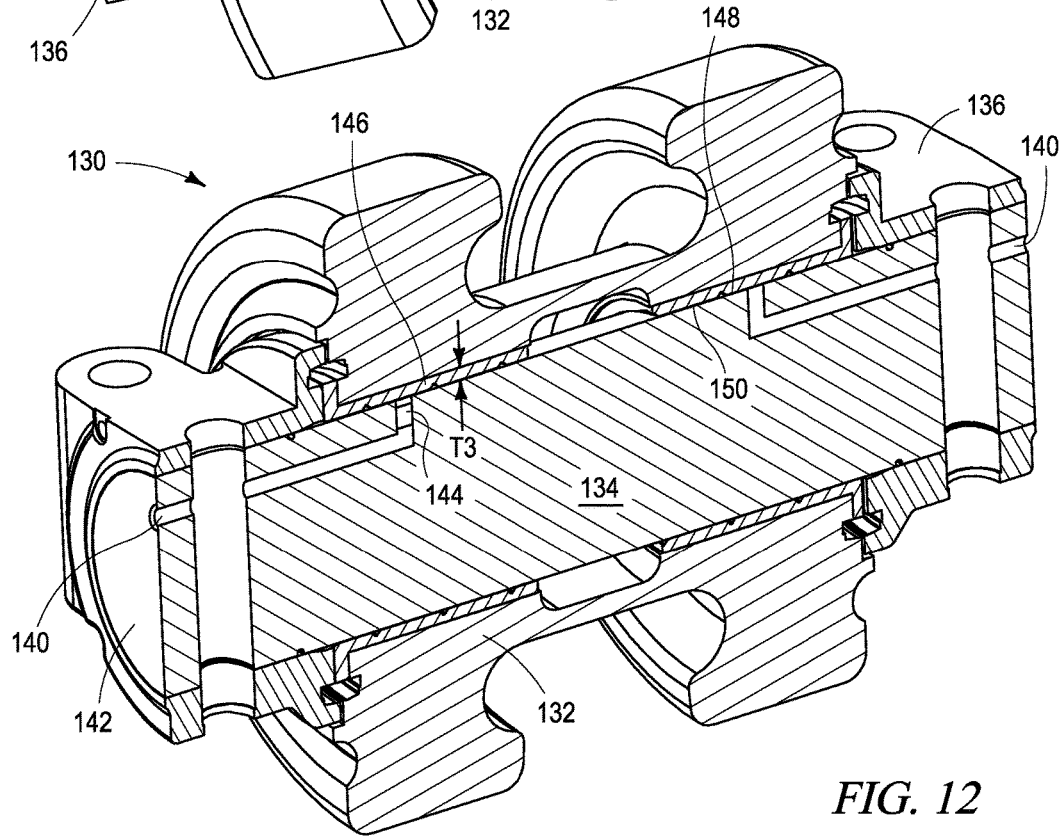
FIG. 12 illustrates a cross section of an alternative roller assembly with a monitoring device disposed within the shaft.

FIG. 12 shows a cross section of an alternative roller assembly 130 with a monitoring device disposed within the shaft. Openings 140 are formed through each end 142 of shaft 134. Monitoring device 144 fits within opening 140 and is mounted within shaft 134. Monitoring device 144 monitors the operational state of bushings 146.

Bushings 146 are pressed into roller body 132 such that bushings 146 are fixed within roller body 132. Bushings 146 are rigidly affixed to the inner surface of roller body 132. Roller body 132 and bushings 146 rotate together around shaft 134, and therefore, are dynamic with respect to shaft 134. Bushings 146 are disposed within roller assembly 130 to reduce the friction between roller body 132 and shaft 134. Bushing 146 allows roller body 132 to turn or rotate around shaft 134 without damaging roller body 132, bushings 146, or shaft 134. Bushings 146 includes inner surface 148 which contacts shaft 134. Bushing 146 can be metal, including copper, tin, zinc, nickel, iron, aluminum, or other metal or can be metal alloy such as copper and tin, known as bronze, copper and zinc, or other metal alloy. In one embodiment, bushing 146 is bronze, a nonferrous metal, and is a softer metal than roller body 132 and shaft 134. A lubricant is disposed between shaft 134 and surface 148 of bushing 146 to reduce the friction between shaft 134 and surface 148 of bushing 146. In a self-contained lubrication system, lubricant is sealed inside roller assembly 130.

Openings 140 are formed partially through each end 142 of shaft 134. Openings 140 are formed parallel to the length of shaft 134 at a depth sufficient to overlap bushing 146. Openings 140 include a portion that is oriented outwards toward a surface of shaft 134. Openings 140 thereby reach surface 150 of shaft 134 at a portion of shaft 134 near bushings 146. Alternatively, openings 140 do not reach surface 150 of shaft 134, but are formed through surface 142 of shaft 134 extending partially though shaft 134. Openings 140 may include a portion parallel to the length of shaft 134 formed completely through shaft 134.

Monitoring device 144 is disposed within opening 140. Monitoring device 144 includes one or more sensors to measure one or more physical characteristics of bushing 146, roller body 132, shaft 134, and the lubricant. Opening 140 is formed with a diameter appropriate to fit monitoring device 144. In one embodiment, the diameter of opening 140 is approximately 1.8 centimeters (cm), or 0.7 inches. In an alternative embodiment, opening 140 can be formed with a diameter greater than or less than 1.8 cm. Opening 140 is formed with a diameter large enough to accommodate monitoring device 144. Opening 140 is formed such that opening 140 does not degrade the strength and functionality of shaft 134.

A monitoring device 144 is placed within each of openings 140 in close proximity to bushings 146. Monitoring device 144 may include one sensor or multiple sensors. In one embodiment, multiple sensors are accommodated within monitoring device 144 which is formed into one unit and fits within openings 140. In an alternative embodiment, additional openings similar to openings 140 are formed through shaft 134 to accommodate multiple monitoring devices 144 or multiple sensors or components of monitoring device 144. In another embodiment, components of monitoring device 144 are disposed on or within bushing 146, roller body 132, or end caps 136. Monitoring device 144 can be incorporated into a lubrication system in order to monitor the lubrication within roller assembly 130. Alternatively, monitoring device 144 is separate from the lubrication system and can be incorporated into existing roller assemblies.

Monitoring device 144 monitors a physical characteristic of roller assembly 130 in order to detect a problem within roller assembly 130. Monitoring device 144 measures temperature of roller assembly 130 and thickness of bushing 146, determines the presence or absence of lubricant within roller assembly 130, and determines if bushing 146 has been worn completely away. Monitoring device 144 includes a sensor such as a Hall effect sensor, temperature sensor, particulate sensor, viscosity sensor, depth sensor, or other type of sensor. In one embodiment, monitoring device 144 measures a temperature at a surface of bushing 146 or a temperature within shaft 134. In an alternative embodiment, monitoring device 144 measures thickness of bushing 146 using a magnet and a Hall effect sensor. In another embodiment, monitoring device 144 includes both a temperature sensor and a Hall effect sensor with a magnet. The temperature sensor, Hall effect sensor, and magnet of monitoring device 144 fit within openings 140 in each end 142 of shaft 134 respectively. Shaft 134 can be configured with additional openings or ports to accommodate additional sensors and other components of monitoring device 144.

In one embodiment of monitoring device 144, a temperature sensor is used to determine the lubricant status within roller assembly 130. Increased temperature within roller assembly 130 is one indicator of inadequate lubrication of bushing 146. A temperature sensor is disposed within or mounted to roller assembly 130 to measure the temperature of roller assembly 130 within roller body 132. When lubrication runs low or runs out, the friction between surface 150 of shaft 134 and inner surface 148 of bushing 146 increases. Without lubricant, surface 150 of shaft 134 directly contacts inner surface 148 of bushing 146. Shaft 134 and bushing 146 are metal, resulting in metal on metal contact. The increased friction between shaft 134 and bushing 146 results in increased temperature at shaft 134 and bushing 146 within roller assembly 130. The change in temperature caused by reduced lubrication or a lack of lubrication is detected by the temperature sensor of monitoring device 144. The temperature sensor may include a contact sensor, such as a thermocouple, thermistor, resistance temperature detector (RTD), or a non-contact temperature sensor, such as an infrared heat sensor. In an alternative embodiment, monitoring device 144 measures the viscosity of the lubricant to determine the quality of lubrication within roller assembly 130. In another embodiment, monitoring device 144 includes a particulate sensor to determine the quality of lubrication and amount of metal particulates within roller assembly 130.

Figure 13:
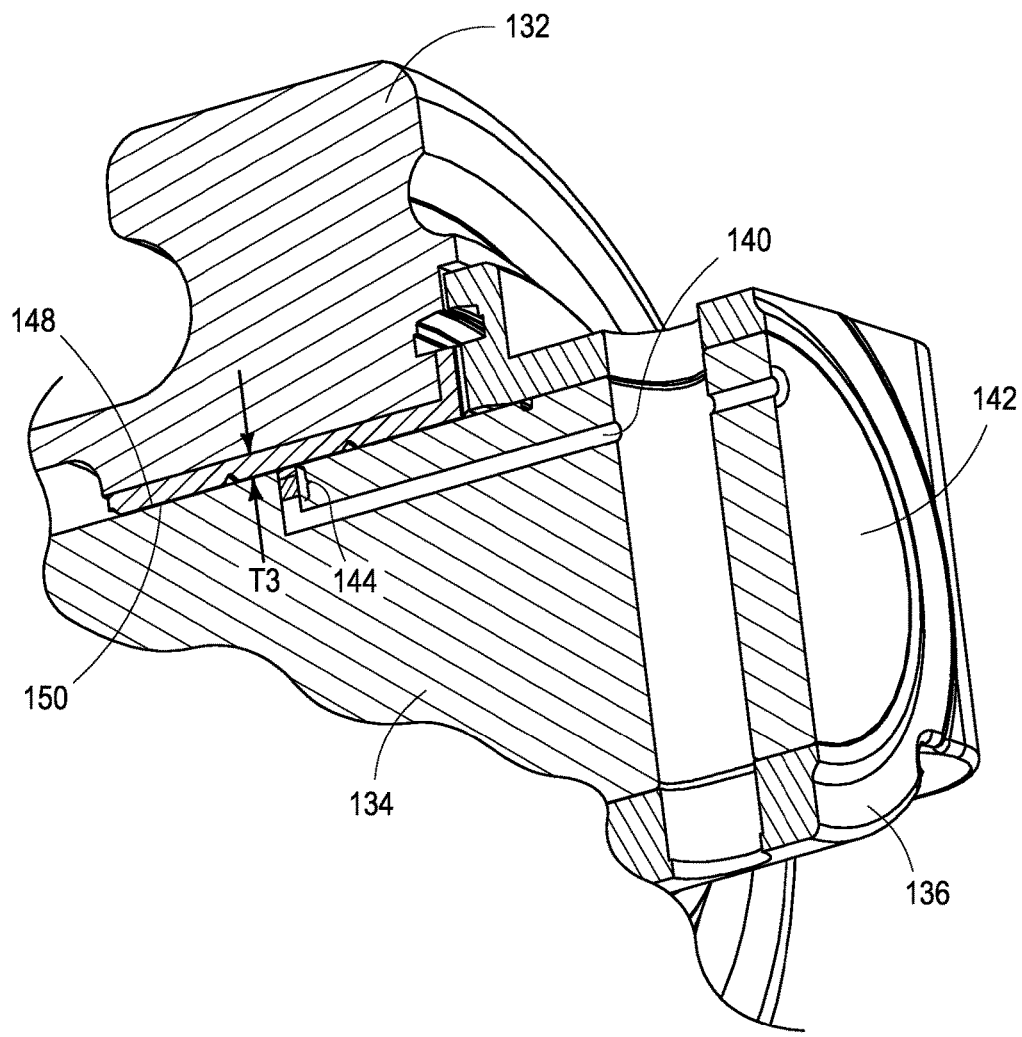
FIG. 13 illustrates further detail of a cross section of an alternative roller assembly with a monitoring device disposed within the shaft.

FIG. 13 illustrates further detail of a cross section of an alternative roller assembly with a monitoring device disposed within the shaft. In one embodiment of monitoring device 144, Hall effect sensor 92 is used to measure a thickness of bushing 146 to determine the amount of wear on bushing 146. Monitoring device 144 includes magnet 90 and Hall effect sensor 92. Hall effect sensor 92 is disposed within opening 140. Magnet 90 is disposed within opening 140 over Hall effect sensor 92 such that Hall effect sensor 92 is disposed between magnet 90 and bushing 146. Bushing 146 is disposed between Hall effect sensor 92 and roller body 132. Hall effect sensor 92 responds to the magnetic field between magnet 90 and roller body 132. In roller assembly 130, bushing 146 is typically bronze, a similar copper alloy, or other alloy or metal. Roller body 132 is typically hardened steel, or other type of steel or metal. Therefore, roller body 132 responds to magnet 90 and bushing 146 is unaffected by magnet 90. The magnetic field between magnet 90 and roller body 132 is uninterrupted by the non-ferrous bushing 146 in between magnet 90 and roller body 132. The distance between roller body 132 and magnet 90 determines a magnetic field at Hall effect sensor 92 which is converted into a voltage by Hall effect sensor 92. The thickness T3 of bushing 146 determines the distance between roller body 132 and magnet 90 because bushing 146 separates roller body 132 from shaft 134 where magnet 90 is located. The magnetic field between roller body 132 and magnet 90 changes when bushing 146 wears down and becomes thinner and roller body 132 moves closer to or farther away from magnet 90. Therefore, monitoring device with magnet 90 and Hall effect sensor 92 detects the amount of wear on bushing 146 by indirectly measuring the thickness of bushing 146.

In an alternative embodiment of monitoring device 144, Hall effect sensor 92 is disposed on one side of bushing 146 and magnet 90 is disposed on a side of bushing 146 opposite the side where Hall effect sensor 92 is disposed. Bushing 146 is disposed between magnet 90 and Hall effect sensor 92. The magnetic field of magnet 90 passes through bushing 146 and is sensed by Hall effect sensor 92. For example, Hall effect sensor 92 is disposed within opening 140 and magnet is not disposed within opening 140, but is disposed in an opening formed through roller body 132 or is disposed on or within bushing 146. As the thickness of bushing 146 changes, the position of Hall effect sensor 92 changes with respect to magnet 90. As Hall effect sensor 92 moves closer or is positioned closer to magnet 90, the magnetic field increases and the voltage produced by Hall effect sensor 92 increases. As Hall effect sensor 92 moves farther from or is positioned farther away from magnet 90, the magnetic field decreases and the voltage produced by Hall effect sensor 92 decreases. Therefore, monitoring device with magnet 90 and Hall effect sensor 92 detects the amount of wear on bushing 146 by directly measuring the thickness of bushing 146. In each embodiment, monitoring device 144 functions even while roller body 132 is moving or rotating. Monitoring device 144 produces output data which indicates the bushing thickness thereby reporting an operational state of bushing 132 in real-time.

The temperature sensor and Hall effect sensor 92 within monitoring device 144 produce output signals or output data. The output from monitoring device 144 is transferred to an external receiving device which processes the signals or data output. A transmitter or connection port is used to transfer signal or data output from monitoring device 144 to an external receiving device, such as a computer. The transmitted data can then be uploaded to a computer or other device which processes the data. Data from monitoring device 144 is used to monitor the operational condition of roller assembly 130 while roller assembly 130 is in use. Real-time monitoring of roller assembly 130 allows problems with lubricant and bushings to be addressed earlier and before damage to roller assembly 130 occurs.

Real-time monitoring of roller assembly 130 allows problems with lubricant and bushings to be addressed earlier and before damage to roller assembly 130 occurs. An operator is alerted when lubricant runs dry and stop the equipment before roller body 132 quickly wears through bushing 146 causing premature failure of roller assembly. Lubricant can simply be replaced or a lubrication system repaired, rather than replacing an entire damaged roller assembly. Bushing wear can be monitored regularly and bushings 146 can be replaced before bushings 146 are worn completely through and roller body 132 begins to grind into shaft 132. Bushings can be replaced before damage to roller assembly 130 is too substantial to be repaired. Monitoring device 144 thereby provides a preventative monitoring and maintenance tool that reduces maintenance costs in track undercarriages by detecting roller problems early and preventing premature roller failure.

Figure 14:
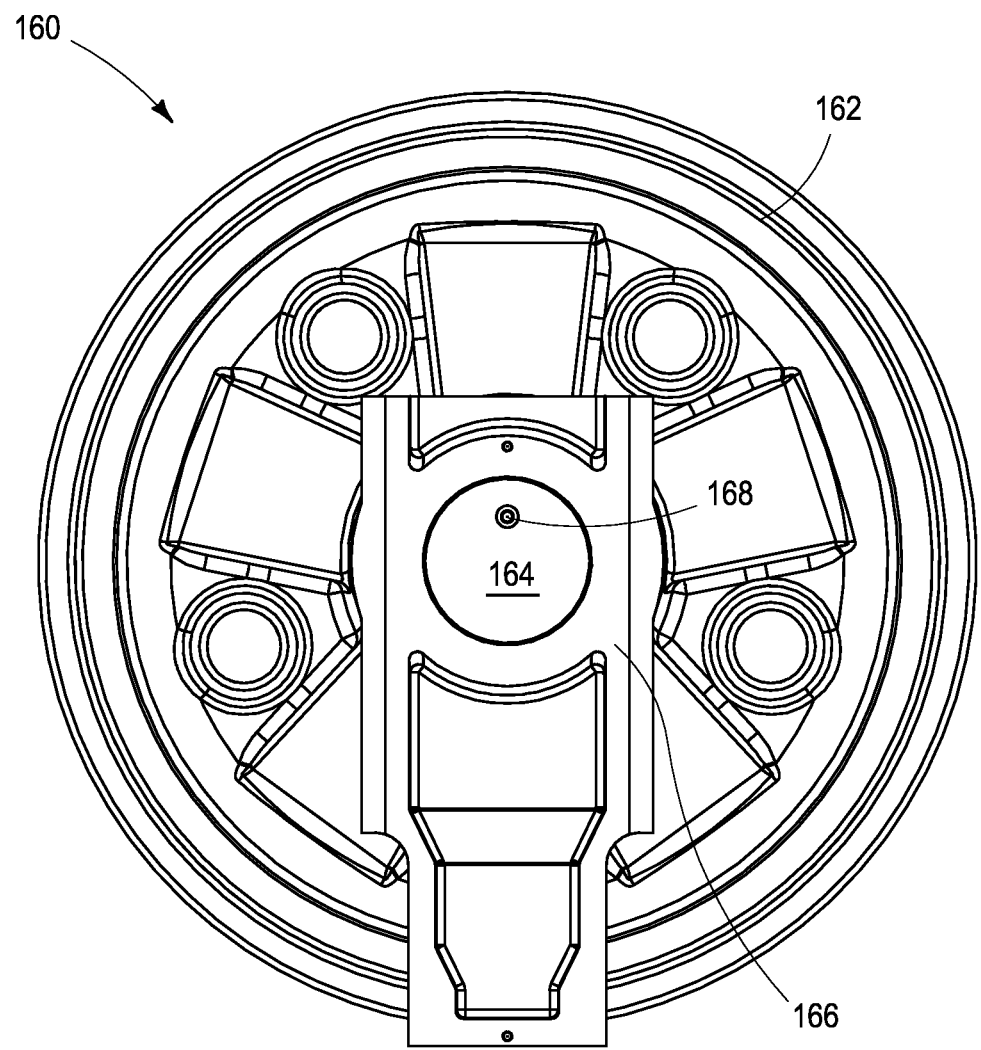
FIG. 14 illustrates an alternative embodiment of a roller assembly with an idler roller and including a monitoring device.

FIG. 14 illustrates an alternative embodiment of a roller assembly with an idler roller and including a monitoring device. Idler roller assembly 160 constitutes a roller and includes idler body 162, shaft 164, end caps 166, and bushings. Idler body 162 rotates around shaft 164. Idler body 162 can be metal, such as high strength steel, hardened steel, carbon steel, metal alloy, or other metal. In one embodiment, idler body 162 is hardened steel. Idler body 162 is monitored with the monitoring device disposed within the roller assembly to detect wear within the roller assembly before idler body 162 is damaged. Idler body 162 rotates around fixed shaft 164. Shaft 164 is fixed within end caps 166. End caps 166 are rigidly attached to or mounted to the undercarriage frame and idler body 162 and shaft 164 are mounted to the undercarriage frame by end caps 166. End caps 166 can be metal, including high strength steel, hardened steel, carbon steel, metal alloy, or other metal. Opening 168 is formed through surface 170 of shaft 164 to provide a mounting point for a monitoring device.

Figure 15:
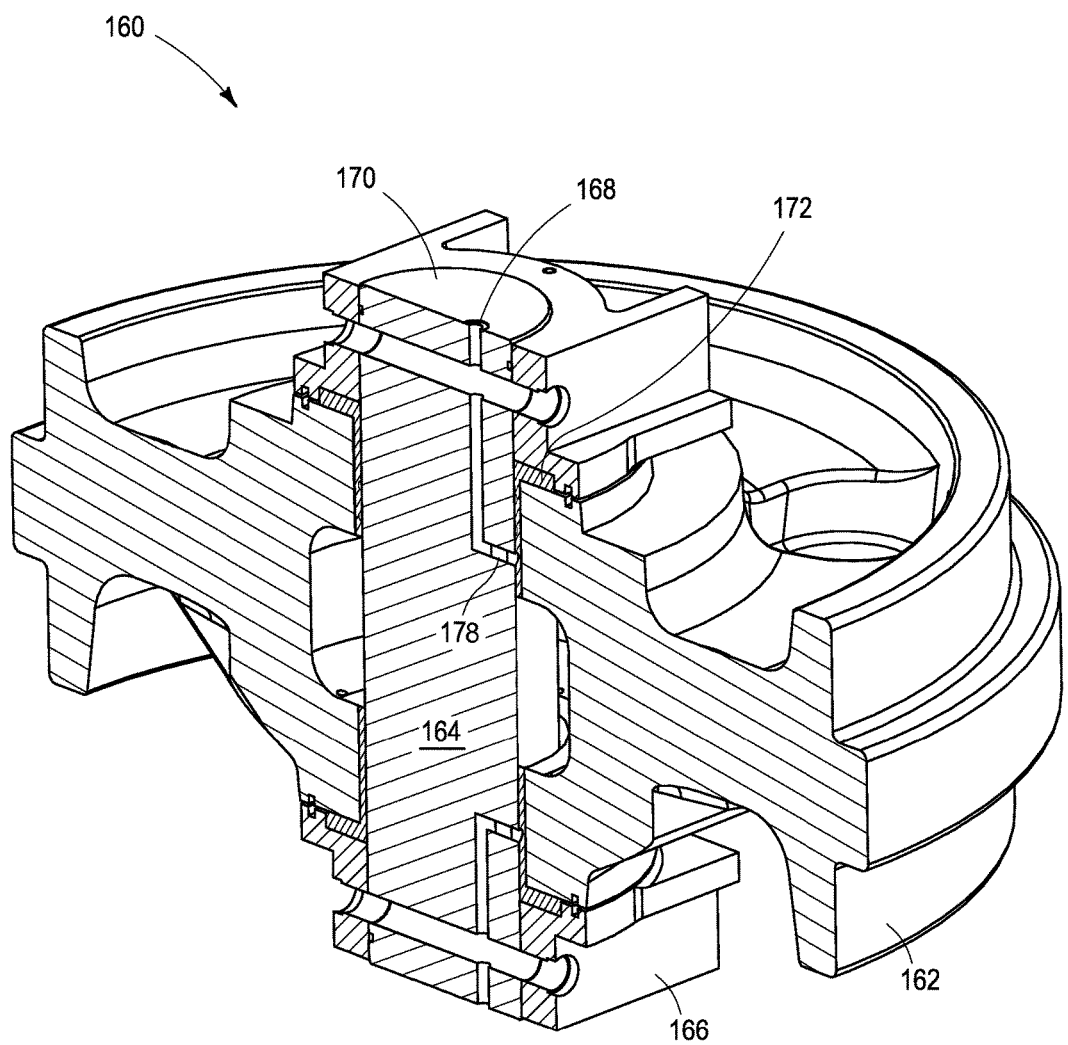
FIG. 15 illustrates a cross section of an idler roller including a monitoring device.

FIG. 15 illustrates a cross section of an idler roller including a monitoring device. Bushings 172 are pressed into idler body 162 such that bushings 172 are fixed within idler body 162. Bushings 172 are rigidly affixed to the inner surface of idler body 162. Idler body 162 and bushings 172 rotate together around shaft 164, and therefore, are dynamic with respect to shaft 164. Bushings 172 are disposed within idler body 162 to reduce the friction between idler body 162 and shaft 164. Bushing 172 allows idler body 162 to turn or rotate around shaft 164 without damaging idler body 162, bushings 172, or shaft 164. Bushings 172 includes inner surface 174 which contacts shaft 164. Bushing 172 can be metal, including copper, tin, zinc, nickel, iron, aluminum, or other metal or can be metal alloy such as copper and tin, known as bronze, copper and zinc, or other metal alloy. In one embodiment, bushing 172 is bronze, a nonferrous metal, and is a softer metal than idler body 162 and shaft 164. A lubricant is disposed between shaft 164 and bushing 172 to reduce the friction between shaft 164 and bushing 172. In a self-contained lubrication system, lubricant is sealed inside roller assembly 160.

Openings 168 are formed partially through each end 170 of shaft 164. Openings 168 are formed parallel to the length of shaft 164 at a depth sufficient to overlap bushing 172. Openings 168 include a portion that is oriented outwards toward a surface of shaft 164. Openings 168 thereby reach surface 176 of shaft 164 at a portion of shaft 164 near bushings 172. Alternatively, openings 168 do not reach surface 176 of shaft 164, but are formed through surface 170 of shaft 164 extending partially though shaft 164. Openings 168 may include a portion parallel to the length of shaft 164 formed completely through shaft 164.

Monitoring device 178 is disposed within opening 168. Monitoring device 178 includes one or more sensors to measure one or more physical characteristics of bushing 172, idler body 162, shaft 164, and the lubricant. Opening 168 is formed with a diameter appropriate to fit monitoring device 178. In one embodiment, the diameter of opening 168 is approximately 1.8 centimeters (cm), or 0.7 inches. In an alternative embodiment, opening 168 can be formed with a diameter greater than or less than 1.8 cm. Opening 168 is formed with a diameter large enough to accommodate monitoring device 178. Opening 168 is formed such that opening 168 does not degrade the strength and functionality of shaft 164.

A monitoring device 178 is placed within each of openings 168 in close proximity to bushings 172. Monitoring device 178 may include one sensor or multiple sensors. In one embodiment, multiple sensors are accommodated within monitoring device 178 which is formed into one unit and fits within openings 168. In an alternative embodiment, additional openings similar to openings 168 are formed through shaft 164 to accommodate multiple monitoring devices 178 or multiple sensors or components of monitoring device 178. In another embodiment, components of monitoring device 178 are disposed on or within bushing 172, roller body 162, or end caps 166. Monitoring device 178 can be incorporated into a lubrication system in order to monitor the lubrication within roller assembly 160. Alternatively, monitoring device 178 is separate from the lubrication system and can be incorporated into existing roller assemblies.

Monitoring device 178 monitors a physical characteristic of roller assembly 160 in order to detect a problem within roller assembly 160. Monitoring device 178 measures temperature of roller assembly 160 and thickness of bushing 172, determines the presence or absence of lubricant within roller assembly 160, and determines if bushing 172 has been worn completely away. Monitoring device 178 includes a sensor such as a Hall effect sensor, temperature sensor, particulate sensor, viscosity sensor, depth sensor, or other type of sensor. In one embodiment, monitoring device 178 measures a temperature at a surface of bushing 172 or a temperature within shaft 164. In an alternative embodiment, monitoring device 178 measures thickness of bushing 172 using a magnet and a Hall effect sensor. In another embodiment, monitoring device 178 includes both a temperature sensor and a Hall effect sensor with a magnet. The temperature sensor, Hall effect sensor, and magnet of monitoring device 178 fit within openings 168 in each end 170 of shaft 164 respectively. Shaft 164 can be configured with additional openings or ports to accommodate additional sensors and other components of monitoring device 178.

In one embodiment of monitoring device 178, a temperature sensor is used to determine the lubricant status within roller assembly 160. Increased temperature within roller assembly 160 is one indicator of inadequate lubrication of bushing 172. A temperature sensor is disposed within or mounted to roller assembly 160 to measure the temperature of roller assembly 160 within idler body 162. When lubrication runs low or runs out, the friction between surface 176 of shaft 164 and inner surface 174 of bushing 172 increases. Without lubricant, surface 176 of shaft 164 directly contacts inner surface 174 of bushing 172. Shaft 164 and bushing 172 are metal, resulting in metal on metal contact. The increased friction between shaft 164 and bushing 172 results in increased temperature at shaft 164 and bushing 172 within roller assembly 160. The change in temperature caused by reduced lubrication or a lack of lubrication is detected by the temperature sensor of monitoring device 178. The temperature sensor may include a contact sensor, such as a thermocouple, thermistor, resistance temperature detector (RTD), or a non-contact temperature sensor, such as an infrared heat sensor. In an alternative embodiment, monitoring device 178 measures the viscosity of the lubricant to determine the quality of lubrication within roller assembly 160. In another embodiment, monitoring device 178 includes a particulate sensor to determine the quality of lubrication and amount of metal particulates within roller assembly 160.

Figure 16:
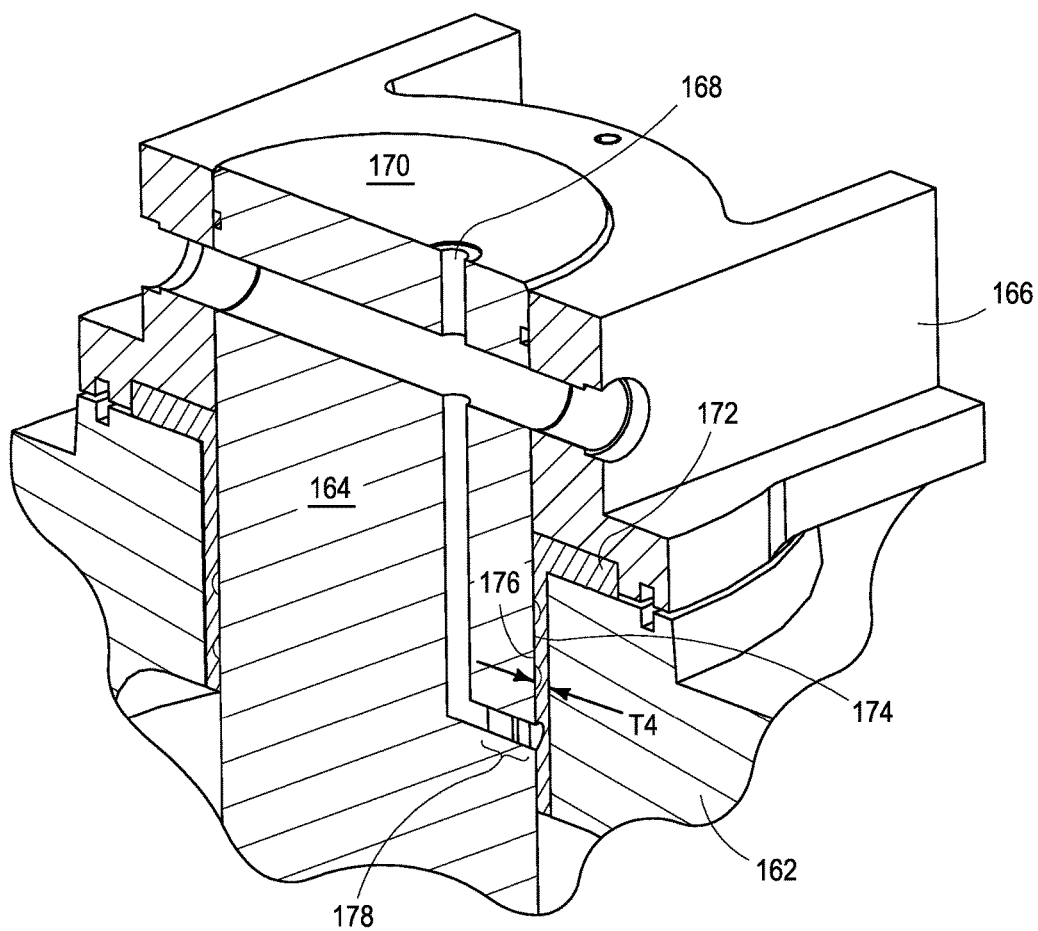
FIG. 16 illustrates further detail of a cross section of an idler roller including a monitoring device.

FIG. 16 illustrates further detail of a cross section an idler roller including a monitoring device. In one embodiment of monitoring device 178, Hall effect sensor 92 is used to measure a thickness of bushing 172 to determine the amount of wear on bushing 172. Monitoring device 178 includes magnet 90 and Hall effect sensor 92. Hall effect sensor 92 is disposed within opening 168. Magnet 90 is disposed within opening 168 over Hall effect sensor 92 such that Hall effect sensor 92 is disposed between magnet 90 and bushing 172. Bushing 172 is disposed between Hall effect sensor 92 and idler body 162. Hall effect sensor 92 responds to the magnetic field between magnet 90 and idler body 162. In roller assembly 160, bushing 172 is typically bronze, a similar copper alloy, or other alloy or metal. Idler roller body 162 is typically hardened steel, or other type of steel or metal. Therefore, idler body 162 responds to magnet 90 and bushing 172 is unaffected by magnet 90. The magnetic field between magnet 90 and idler body 162 is uninterrupted by the non-ferrous bushing 172 in between magnet 90 and idler body 162. The distance between idler body 162 and magnet 90 determines a magnetic field at Hall effect sensor 92 which is converted into a voltage by Hall effect sensor 92. The thickness of bushing 172 determines the distance between idler body 162 and magnet 90 because bushing 172 separates idler body 162 from shaft 164 where magnet 90 is located. The magnetic field between idler body 162 and magnet 90 changes when bushing 172 wears down and becomes thinner and idler body 162 moves closer to or farther away from magnet 90. Therefore, monitoring device with magnet 90 and Hall effect sensor 92 detects the amount of wear on bushing 172 by indirectly measuring the thickness of bushing 172.

In an alternative embodiment of monitoring device 178, Hall effect sensor 92 is disposed on one side of bushing 172 and magnet 90 is disposed on a side of bushing 172 opposite the side where Hall effect sensor 92 is disposed. Bushing 172 is disposed between magnet 90 and Hall effect sensor 92. The magnetic field of magnet 90 passes through bushing 172 and is sensed by Hall effect sensor 92. For example, Hall effect sensor 92 is disposed within opening 168 and magnet is not disposed within opening 168, but is disposed in an opening formed through roller body 162 or is disposed on or within bushing 174. As the thickness of bushing 172 changes, the position of Hall effect sensor 92 changes with respect to magnet 90. As Hall effect sensor 92 moves closer or is positioned closer to magnet 90, the magnetic field increases and the voltage produced by Hall effect sensor 92 increases. As Hall effect sensor 92 moves farther from or is positioned farther away from magnet 90, the magnetic field decreases and the voltage produced by Hall effect sensor 92 decreases. Therefore, monitoring device with magnet 90 and Hall effect sensor 92 detects the amount of wear on bushing 172 by directly measuring the thickness of bushing 172. In each embodiment, monitoring device 178 functions even while roller body 162 is moving or rotating. Monitoring device 178 produces output data which indicates the bushing thickness thereby reporting an operational state of bushing 172 in real-time.

The temperature sensor and Hall effect sensor 92 within monitoring device 178 produce output signals or output data. The output from monitoring device 178 is transferred to an external receiving device which processes the signals or data output. A transmitter or connection port is used to transfer signal or data output from monitoring device 178 to an external receiving device, such as a computer. The transmitted data can then be uploaded to a computer or other device which processes the data. Data from monitoring device 178 is used to monitor the operational condition of roller assembly 160 while roller assembly 160 is in use. Real-time monitoring of roller assembly 160 allows problems with lubricant and bushings to be addressed earlier and before damage to roller assembly 160 occurs.

Real-time monitoring of roller assembly 160 allows problems with lubricant and bushings to be addressed earlier and before damage to roller assembly 160 occurs. An operator is alerted when lubricant runs dry and stop the equipment before roller body 162 quickly wears through bushing 172 causing premature failure of roller assembly. Lubricant can simply be replaced or a lubrication system repaired, rather than replacing an entire damaged roller assembly. Bushing wear can be monitored regularly and bushings 172 can be replaced before bushings 172 are worn completely through and roller body 162 begins to grind into shaft 162. Bushings can be replaced before damage to roller assembly 160 is too substantial to be repaired. Monitoring device 178 thereby provides a preventative monitoring and maintenance tool that reduces maintenance costs in track undercarriages by detecting roller problems early and preventing premature roller failure.

While one or more embodiments of the present invention have been illustrated in detail, the skilled artisan will appreciate that modifications and adaptations to those embodiments may be made without departing from the scope of the present invention as set forth in the following claims.

What is claimed is:

1. An undercarriage monitoring device, comprising:
   a roller assembly of a track-type undercarriage including,
      a roller housing mounted to a frame of the track-type undercarriage, and
      a roller including a ferrous material and an end of the roller extending into the roller housing, the roller configured to rotate with respect to the roller housing;
   a bushing comprising a non-ferrous material and press fit into the roller housing;
   a Hall effect sensor disposed in an opening of the roller housing, wherein the non-ferrous material of the bushing contacts the Hall effect sensor and extends uninterrupted as a uniform body of material from the Hall effect sensor to the roller; and
   a magnet disposed in the opening of the roller housing over the Hall effect sensor.

2. The undercarriage monitoring device of claim 1, further including a data transmitting device in the opening of the roller housing and coupled to the Hall effect sensor.

3. The undercarriage monitoring device of claim 1, further including a temperature sensor disposed on the roller housing.

4. The undercarriage monitoring device of claim 1, wherein the bushing consists of the non-ferrous material.

5. The undercarriage monitoring device of claim 1, further including a lubricant disposed between the bushing and roller.

6. The undercarriage monitoring device of claim 1, wherein each of the bushings further includes a channel in an inner surface of the bushing.

7. An undercarriage monitoring device, comprising:
   an undercarriage including,
      an undercarriage frame,
      a roller housing mounted to the undercarriage frame,
      a roller including a ferrous material and an end of the roller extending into the roller housing,
      a bushing including a non-ferrous material press fit into the roller housing, wherein the non-ferrous material of the bushing extends from the roller housing to the roller for an entire circumference of the bushing,
      a Hall effect sensor disposed in an opening of the roller housing, wherein the Hall effect sensor contacts the bushing through the opening of the roller housing, and
      a track including a series of individual track shoes linked together in a continuous chain around the roller.

8. The undercarriage of claim 7, wherein the bushing further includes:
   an inner cylindrical surface contacting the roller; and
   an outer cylindrical surface contacting the roller housing, wherein the non-ferrous material substantially fills an area between the inner cylindrical surface and outer cylindrical surface.

9. The undercarriage of claim 8, wherein the inner cylindrical surface and outer cylindrical surface of the bushing are in fixed rotational alignment relative to the roller housing, and the end of the roller is configured to rotate within the bushing.

10. The undercarriage of claim 7, further including a lubricant disposed between the bushing and roller.

11. The undercarriage of claim 7, wherein the bushing further includes a channel in an inner surface of the bushing.

12. The undercarriage of claim 7, wherein the Hall effect sensor is configured to generate a voltage potential proportional to a distance between the Hall effect sensor and the roller.

13. A method of monitoring an undercarriage, comprising:
   providing a roller assembly of an undercarriage including,
      a fixed roller component, and
      a rotating roller component comprising a ferrous material;
   disposing a bushing comprising a non-ferrous material between the fixed roller component and the rotating roller component, wherein the non-ferrous material of the bushing extends continuously from the fixed roller component to the rotating roller component;
   disposing a Hall effect sensor on the fixed roller component adjacent to the bushing; and
   determining wear on the bushing by measuring a thickness of the bushing using the Hall effect sensor.

14. The method of claim 13, further including:
   collecting data from the Hall effect sensor; and
   transmitting the data from the Hall effect sensor to a receiving device.

15. The method of claim 13, further including:
forming an opening in the fixed roller component; and
disposing the Hall effect sensor within the opening in the fixed roller component.

16. The method of claim 13, further including measuring the thickness of the bushing using the Hall effect sensor while the roller assembly is operating.

17. The method of claim 13, further including determining a distance between the fixed roller component and rotating roller component by using the Hall effect sensor to measure a magnetic field.

18. The method of claim 17, wherein the distance between the fixed roller component and rotating roller component is equivalent to a solid thickness of the non-ferrous material of the bushing, wherein the entire solid thickness of non-ferrous material is held together through metallic bonds of the non-ferrous material.

19. An undercarriage comprising:
a roller housing;
a bushing including a non-ferrous material press fit into the roller housing;
a Hall effect sensor disposed in the roller housing, the Hall effect sensor configured to detect a wear of the bushing based on a thickness of the bushing;
a roller including a ferrous material and an end of the roller extending into the roller housing, wherein the non-ferrous material of the bushing extends continuously from the roller housing to the roller; and
a data processor disposed in communication with the Hall effect sensor, wherein the data processor is located remote to the Hall effect sensor and is configured to provide an alert based on the wear of the bushing.

20. The undercarriage of claim 19, wherein the Hall effect sensor is configured to detect the wear of the bushing while the undercarriage is operating.

21. The undercarriage of claim 19, wherein the Hall effect sensor is configured to generate a voltage potential proportional to a distance between the Hall effect sensor and the roller.

22. The undercarriage of claim 19, further including a magnet disposed on an opposite side of the bushing from the Hall effect sensor.

23. The undercarriage of claim 19, wherein the bushing further includes:
an inner cylindrical surface contacting the roller; and
an outer cylindrical surface contacting the roller housing, wherein the non-ferrous material substantially fills an entire area between the inner cylindrical surface and outer cylindrical surface.

24. The undercarriage of claim 23, wherein the inner cylindrical surface and outer cylindrical surface of the bushing are in fixed rotational alignment relative to the roller housing, and the end of the roller is configured to rotate against the inner cylindrical surface of the bushing.

25. The undercarriage of claim 24, further including a lubricant disposed between the roller and the inner cylindrical surface of the bushing.

* * * * *